(12) United States Patent
Thompson et al.

(10) Patent No.: US 7,435,820 B2
(45) Date of Patent: Oct. 14, 2008

(54) SUBSTITUTED TETRAHYDRO-1H-PYRAZOLO[3,4-C]PYRIDINES COMPOSITIONS COMPRISING THEM, AND USE

(75) Inventors: Fabienne Thompson, Paris (FR); Catherine Souaille, Choisy le Roi (FR); Fabrice Viviani, Louvres (FR); Michel Tabart, La Norville (FR); Patrick Mailliet, Fontenay Sous Bois (FR); Teresa Damiano, Paris (FR); Marie-Pierre Cherrier, Ivy sur Seine (FR); Francois Clerc, Antony (FR); Frank Halley, Sevres (FR); Herve Bouchard, Thiais (FR); Laurence Gauzy-Lazo, Paris (FR); Bernard Baudoin, Chaville (FR)

(73) Assignee: Aventis Pharma S.A., Antony (FR)

( * ) Notice: Subject to any disclaimer, the term of this patent is extended or adjusted under 35 U.S.C. 154(b) by 169 days.

(21) Appl. No.: 11/419,794

(22) Filed: May 23, 2006

(65) Prior Publication Data

US 2006/0199837 A1 Sep. 7, 2006

Related U.S. Application Data

(62) Division of application No. 10/888,611, filed on Jul. 9, 2004, now Pat. No. 7,109,340.

(30) Foreign Application Priority Data

Jul. 10, 2003 (FR) ................... 03 08441
Jul. 10, 2003 (FR) ................... 03 08442

(51) Int. Cl.
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. ...................... 546/119; 546/120

(58) Field of Classification Search .............. 546/119, 546/120; 514/303
See application file for complete search history.

(56) References Cited

FOREIGN PATENT DOCUMENTS

| FR | 2827861 | | 1/2003 |
|---|---|---|---|
| WO | 02/12242 | * | 2/2002 |
| WO | WO 02/12242 | | 2/2002 |
| WO | WO 03/024967 | | 3/2003 |
| WO | WO 2004/064778 | | 8/2004 |

OTHER PUBLICATIONS

Hetian et al., The journal of biological chemistry, 2002, vol. 277, pp. 43137-43142.*
Dorte Krehan et al., Aza-THIP and Related Analogues of THIP as GABAc Antagonists, Bioorganic & Medicinal Chemistry (2003, pp. 4891-4896, vol. 11).
Povl Krogsgaard-Larsen et al., GABA Agonists. Synthesis and structure-activity studies on analogues of isoguvacine and THIP, Eur. J. Med. Chem.- (1979, pp. 157-167, vol. 14, No. 2).

* cited by examiner

*Primary Examiner*—D. Margaret Seaman
*Assistant Examiner*—Niloofar Rahmani
(74) *Attorney, Agent, or Firm*—Kelly L. Bender; Paul R. Darkes

(57) ABSTRACT

Substituted tetrahydro-1H-pyrazolo[3,4-c]pyridines, compositions comprising them and use. The present invention relates in particular to novel substituted tetrahydro-1H-pyrazolo[3,4-c]pyridines having therapeutic activity, which can be used in particular in oncology.

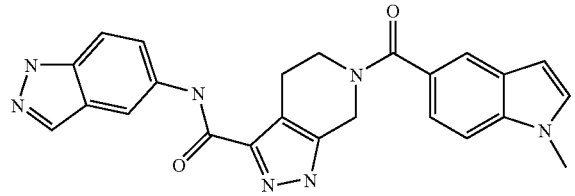

11 Claims, No Drawings

SUBSTITUTED TETRAHYDRO-1H-PYRAZOLO [3,4-C]PYRIDINES COMPOSITIONS COMPRISING THEM, AND USE

CROSS REFERENCE TO RELATED APPLICATIONS

This application is a division of U.S. application Ser. No. 10/888,611, filed Jul. 09, 2004, now allowed, which is incorporated herein by reference in its entirety; and which claims the benefit of priority of French Patent Application No. 03/08, 441, filed Jul. 10, 2003 and French Patent Application No. 03/08,442, filed Jul. 10, 2003.

The present invention relates to novel chemical compounds, particularly novel tetrahydro-1H-pyrazolo[3,4-c]pyridines, compositions comprising the, and to their use as medicinal products.

More particularly, the invention relates to novel tetrahydro-1H-pyrazolo-[3,4-c]pyridines exhibiting anticancer activity, and in particular kinase-inhibiting activity, especially Tie2-inhibiting activity.

Only a few tetrahydro-1H-pyrazolo[3,4-c]pyridines are known.

Thus, WO 02/012442 discloses tetrahydro-1H-pyrazolo[3,4-c]pyridines substituted in the 5-position with an optionally substituted amino group. These products are useful in the treatment of cancer and of other diseases related to cell proliferation.

P. Krogsgaard-Larsen et al. in Eur. J. Med. Chemical—Chim. Ther. (1979), 14(2), p. 157-164, discloses two tetrahydro-1H-pyrazolo[3,4-c]pyridines substituted in the 3-position with a hydroxyl group.

WO 96112720 claims tetrahydro-1H-pyrazolo[3,4-c]pyridines substituted in the 3-position with substituents chosen from H, alkyl, alkylene, cycloalkyl and methylenecycloalkyl, and in the 1- and 6-positions with varied substituents. These products are described as inhibitors (i) of phosphodiesterase type IV (PDE-IV), and (ii) of tumour necrosis factor (TNF), and are, as a result, considered to be useful in the treatment of inflammatory diseases. No example of a compound according to the invention is disclosed.

Attempts to obtain effective inhibitors of Tie2 have already been successful in the past (in this respect, see, for example, WO 98/02434; WO 98/41525; WO 99/10325; WO 99/17770; WO 99/54286; WO 99/21859; WO 99/55335; WO 00/17202; WO 00/17203; WO 00/27822; WO 00/75139; WO 01/37835; WO 01/57008; WO 01/72751; WO 02/060382; WO 02/076396; WO 02/076463; WO 02/076954; WO 02/076984; WO 02/076985; WO 02/080926; WO 03/004488).

However, none of those documents discloses 4,5,6,7-tetrahydro-1H-pyrazolo[3,4-c]pyridine derivatives as defined below, exhibiting activity against kinases, in particular Tie2.

To this effect, the products in accordance with the invention, according to its first aspect, satisfy formula (I) below:

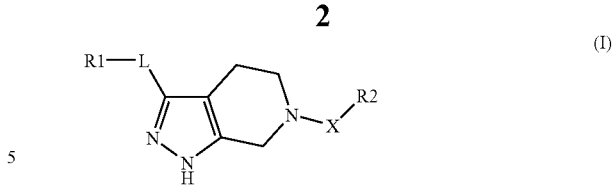

and its tautomers, in which:

L is chosen from a bond, $CH_2$, CO, $SO_2$, CONH, COO, NHCO, NH, $NHSO_2$, $SO_2NH$, NHCONH, $CH_2NH$ and $NHCH_2$;

X is chosen from a bond, $CH_2$, CO, $SO_2$, CONH and COO;

R1 is chosen from OH, H, alkyl, cycloalkyl, heterocyclyl, aryl, heteroaryl, which is optionally substituted, and, when X is a bond, then R1 may also be halogen;

R2 is H or is chosen from alkyl, alkylene, cycloalkyl, heterocyclyl, aryl, heteroaryl, which is optionally substituted;

the substituents being chosen independently from R3, O—R3, halogen, $NO_2$, $SO_2$—R3, CO—R3, $SO_2NH$—R3, CONH—R3, N—$(R3)_2$, NHCO—R3, $NHSO_2$—R3, NHCONH—R3, $NHSO_2NH$—R3, OCO—R3, COO—R3, $OSO_2$—R3, $SO_2O$—R3, OCONH—R3 and $OSO_2NH$—R3, where each R3 is chosen independently from H, alkyl, cycloalkyl, alkenyl, aryl, heteroaryl, heterocyclyl, which is optionally substituted with halogen, aryl, heteroaryl, R4, OR4 or $N(R4)_2$, each R4 being chosen independently from H, $C_1$-$C_4$ alkyl and halogenated $C_1$-$C_4$ alkyl.

Products in accordance with the invention, according to its first aspect, are more particularly chosen from products of formula (II) below:

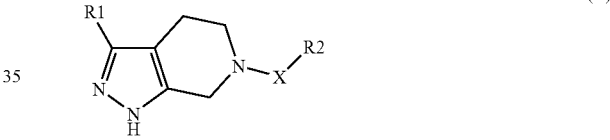

and its tautomers, in which:

X is chosen from a bond, $CH_2$, CO, $SO_2$, CONH and COO;

R1 is chosen from alkyl, cycloalkyl, heterocyclyl, aryl, heteroaryl, which is optionally substituted;

R2 is H or is chosen from alkyl, alkylene, cycloalkyl, heterocyclyl, aryl, heteroaryl, which is optionally substituted;

the substituents being chosen independently from R3, O—R3, halogen, $NO_2$, to $SO_2$—R3, CO—R3, $SO_2NH$—R3, CONH—R3, N—$(R3)_2$, NHCO—R3, $NHSO_2$—R3, NHCONH—R3, $NHSO_2NH$—R3, OCO—R3, COO—R3, $OSO_2$—R3, $SO_2O$—R3, OCONH—R3 and $OSO_2NH$—R3, where each R3 is chosen independently from H, alkyl, cycloalkyl, alkenyl, aryl, heteroaryl, heterocyclyl, which is optionally substituted with halogen, aryl, heteroaryl, R4, OR4 or $N(R4)_2$, where each R4 is chosen independently from H and $C_1$-$C_4$ alkyl.

Products in accordance with the invention, according to its first aspect, are more particularly chosen from products of formula (III) below:

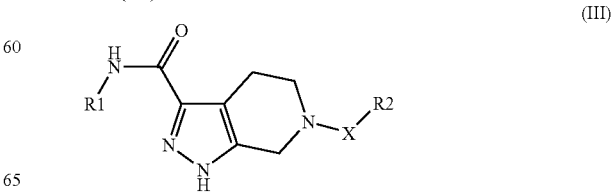

and its tautomers, in which:

X is chosen from a bond, $CH_2$, CO, $SO_2$, CONH and COO;

R1 is chosen from alkyl, cycloalkyl, heterocyclyl, aryl, heteroaryl, which is optionally substituted;

R2 is H or is chosen from alkyl, alkylene, cycloalkyl, heterocyclyl, aryl, heteroaryl, which is optionally substituted;

in which the substituents are chosen independently from R3, O—R3, halogen, $NO_2$, $SO_2$—R3, CO—R3, $SO_2NH$—R3, CONH—R3, N—$(R3)_2$, NHCO—R3, $NHSO_2$—R3, NHCONH—R3, $NHSO_2NH$—R3, OCO—R3, COO—R3, $OSO_2$—R3, $SO_2O$—R3, OCONH—R3 and $OSO_2NH$—R3, in which each R3 is chosen independently from H, alkyl, cycloalkyl, alkenyl, aryl, heteroaryl, heterocyclyl, which is optionally substituted with halogen, aryl, heteroaryl, OR4 or $N(R4)_2$, and in which each R4 is chosen independently from H and $C_1$-$C_4$ alkyl.

A product in accordance with the invention is advantageously chosen from the products according to its first aspect, in which R1 is heteroaryl, which is optionally substituted, in which a preferred heteroaryl is chosen from benzimidazolyl, indolyl, pyrrolyl, optionally substituted with halogen, R4 or O—R4.

More particularly, a preferred heteroaryl is chosen from benzimidazol-2-yl, indol-2-yl, pyrrol-2-yl, optionally substituted with halogen, R4 or O—R4.

A product in accordance with the invention according to its first aspect advantageously has a substituent R2 chosen from phenyl, pyridyl, thienyl, $C_1$-$C_4$ alkyl, and $C_3$-$C_7$ cycloalkyl, which is optionally substituted.

X may advantageously be chosen from CO and $SO_2$.

A product in accordance with the invention according to its first aspect is advantageously chosen from the products of formula (I) in which R1 is H.

A preferred product is advantageously chosen from the products of formula (I) in which R1 is substituted aryl.

According to a first preferred embodiment, a preferred product is advantageously chosen from the products of formula (I) in which R1-L is R1-NH—CO, and more preferably when R1 is H.

Very preferably, and according to a second preferred embodiment, a preferred product is advantageously chosen from (i) the products of formula (I), or (ii) preferably the products according to the first preferred embodiment, in which X is a bond, and in which R2 is chosen from substituted aryl and substituted heteroaryl.

According to a third preferred embodiment, a more preferred product is chosen from the products in accordance with the invention according to its second embodiment, in which R2 is chosen from:

aryl substituted with $NHSO_2$—R3 or NHCONH—R3, and heteroaryl substituted with $NHSO_2$—R3 or NHCONH—R3.

Products according to the third preferred embodiment are advantageously chosen from:

aryl substituted with $NHSO_2$—R3 or NHCONH—R3, and heteroaryl substituted with $NHSO_2$—R3 or NHCONH—R3, in which aryl is phenyl and in which heteroaryl is chosen from pyridyl and pyrimidyl.

According to a fourth embodiment, products according to the third preferred embodiment are advantageously chosen from:

aryl substituted with $NHSO_2$—R3 or NHCONH—R3, and heteroaryl substituted with $NHSO_2$—R3 or NHCONH—R3, in which R3 is chosen from substituted aryl and substituted heteroaryl, in which R3 is advantageously substituted with a substituent selected from the group consisting of halogen, R4, OR4 and $N(R4)_2$, in which each R4 is chosen independently from H, $C_1$-$C_4$ alkyl and halogenated $C_1$-$C_4$ alkyl.

According to a fifth embodiment, products according to the fourth preferred embodiment are advantageously chosen from:

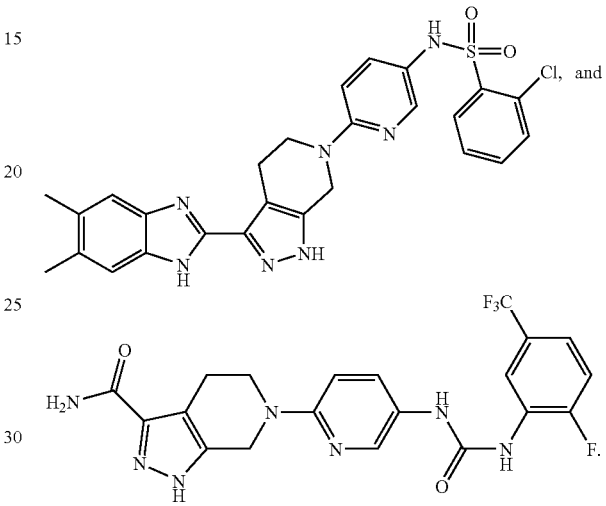

A product in accordance with the invention according to its first aspect may be in:

1) racemic form, or
2) a form enriched in a stereoisomer, or
3) a form enriched in an enantiomer;

and may optionally be salified.

According to a second aspect, the invention relates to pharmaceutical compositions comprising a product as defined above, in combination with a pharmaceutically acceptable excipient.

According to a third aspect, the invention relates to the use of a product as defined above, as an agent for modulating the activity of a kinase. A preferred kinase will advantageously be chosen from Tie2 and KDR. Tie2 is more preferred.

According to its third aspect, the invention relates to the use of a product as defined above, for producing a medicinal product that is useful for treating a pathological condition, in particular cancer.

Products in accordance with the invention can be obtained by methods well known to those skilled in the art, in particular as regards the techniques of coupling between an acid and an amine; see, for example, J. March, Advanced organic chemistry, (J. Wiley & Sons, ed.), fourth edition, 1992.

The products of the invention are useful as agents which inhibit a reaction catalysed by a kinase. Tie2 is a kinase for which the products of the invention will be particularly useful as inhibitors. These products can also be used as inhibitors of other kinases, such as KDR.

Reasons for which the kinases are chosen are given below:

Tie2

Tie-2 (TEK) is a member of a family of tyrosine kinase receptors specific for endothelial cells. Tie2 is the first receptor with tyrosine kinase activity for which both the agonist (angiopoietin 1 or Ang1), which stimulates autophosphorylation of the receptor and cell signalling [S. Davis et al (1996) *Cell* 87, 1161-1169] and the antagonist (angiopoietin 2 or Ang2) [P. C. Maisonpierre et al. (1997) *Science* 277, 55-60] are known. Angiopoietin 1 can synergize with VEGF in the final stages of neoangiogenesis [*Asahara T. Circ. Res.* (1998) 233-240]. Knockout experiments and transgenic manipulations of the expression of Tie2 or of Ang1 result in animals which exhibit vascularization defects [D. J. Dumont et al (1994) *Genes Dev.* 8, 1897-1909 and C. Suri (1996) *Cell* 87, 1171-1180]. The binding of Ang1 to its receptor results in autophosphorylation of the kinase domain of Tie2, which is essential for neovascularization and for the recruitment and the interaction of the vessels with pericytes and smooth muscle cells; these phenomena contribute to the maturing and the stability of the newly formed vessels [P. C. Maisonpierre et al (1997) *Science* 277, 55-60]. Lin et al (1997), *J. Clin. Invest.* 100, 8: 2072-2078 and Lin P. (1998) *PNAS* 95, 8829-8834, have shown inhibition of tumour growth and vascularization and a decrease in lung metastases during adenoviral infections or during injections of the Tie-2 (Tek) extracellular domain in breast tumour and melanoma xenograph models.

Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemoangioma and cancers).

KDR

KDR (Kinase insert Domain Receptor), also known as VEGF-R2 (Vascular Endothelial Growth Factor Receptor 2), is expressed only in endothelial cells. This receptor binds to the angiogenic growth factor VEGF and thus acts as a mediator to a transduction signal via the activation of its intracellular kinase domain. Direct inhibition of kinase activity of VEGF-R2 makes it possible to reduce the phenomenon of angiogenesis in the presence of exogenous VEGF (Vascular Endothelial Growth Factor) (Strawn et al., *Cancer Research*, 1996, vol. 56, p. 3540-3545). This process has been demonstrated in particular using VEGF-R2 mutants (Millauer et al., *Cancer Research*, 1996, vol. 56, p. 1615-1620). The VEGF-R2 receptor does not appear to have any function in adults other than that related to the angiogenic activity of VEGF. Consequently, a selective inhibitor of the kinase activity of VEGF-R2 should only show slight toxicity.

In addition to this central role in the dynamic angiogenic process, recent results suggest that VEGF expression contributes to the survival of tumour cells after chemotherapy and radiotherapy, emphasizing the potential synergy of KDR inhibitors with other agents (Lee et al. *Cancer Research*, 2000, vol. 60, p. 5565-5570).

EXPERIMENTAL SECTION

Method A: Analysis by LC/MS

The LC/MS analyses were carried out on a Micromass model LCT device connected to an HP 1100 device. The abundance of the products was measured using an HP G1315A diode array detector over a wavelength of 200-600 nm and a Sedex 65 light scattering detector. The mass spectra were acquired over a range of from 180 to 800. The data were analysed using the Micromass MassLynx software. Separation was carried out on a Hypersil BDS C18, 3 µm (50×4.6 mm) column, eluting with a linear gradient of from 5 to 90% of acetonitrile comprising 0.05% (v/v) of trifluoroacetic acid (TFA) in water comprising 0.05% (v/v) TFA, over 3.5 min at a flow rate of 1 ml/min. The total analysis time, including the period for re-equilibrating the column, is 7 min.

Method B: Purification by LC/MS:

The products were purified by LC/MS using a Waters FractionsLynx system composed of a Waters model 600 gradient pump, a Waters model 515 regeneration pump, a Waters Reagent Manager dilution pump, a Waters model 2700 autoinjector, two Rheodyne model LabPro valves, a Waters model 996 diode array detector, a Waters model ZMD mass spectrometer and a Gilson model 204 fraction collector. The system was controlled by the Waters FractionLynx software. Separation was carried out alternately on two Waters Symmetry columns ($C_{18}$, 5 µM, 19×50 mm, catalogue reference 186000210), one column undergoing regeneration with a 95/5 (v/v) water/acetonitrile mixture comprising 0.07% (v/v) of trifluoroacetic acid, while the other column was being used for separation. The columns were eluted using a linear gradient of from 5 to 95% of acetonitrile comprising 0.07% (v/v) of trifluoroacetic acid in water comprising 0.07% (v/v) of trifluoroacetic acid, at a flow rate of 10 ml/min. At the outlet of the separation column, one-thousandth of the effluent is separated by means of an LC Packing Accurate, diluted with methyl alcohol at a flow rate of 0.5 ml/min and sent to the detectors, in a proportion of 75% to the diode array detector and the remaining 25% to the mass spectrometer. The rest of the effluent (999/1000) is sent to the fraction collector, where the flow is discarded for as long as the mass of the expected product is not detected by the FractionLynx software. The molecular formulae of the expected products are supplied to the FractionLynx software, which actuates the collection of the product when the mass signal detected corresponds to the ion $[M+H]^+$ and/or to $[M+Na]^+$. In certain cases, depending on the results of the analytical LC/MS, when an intense ion corresponding to $[M+2H]^{++}$ was detected, the value corresponding to half the calculated molecular mass (MW/2) is also supplied to the FractionLynx software. Under these conditions, the collection is also actuated when the mass signal of the ion $[M+2H]^{++}$ and/or $[M+Na+H]^{++}$ are detected.

Method C: EI Analysis

The mass spectra were produced by electron impact (70 eV) on a Finnigan SSQ 7000 spectrometer.

Method D: NMR Analysis
The NMR spectra were produced on a Bruker Avance 300 spectrometer and a Bruker Avance DRX 400 spectrometer.
tert-Butyl 4-(diazoethoxycarbonylmethyl)-4-hydroxypiperidine-1-carboxylate
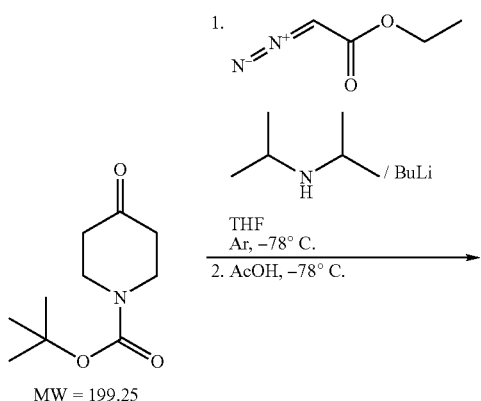
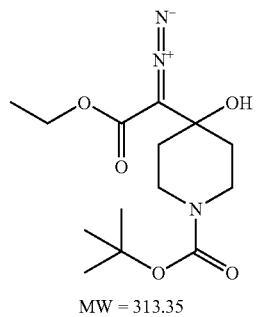
| | CAS | Name | d | MM | eq | mmol | g | ml |
|---|---|---|---|---|---|---|---|---|
| 1 | 79099-07-3 | N-Boc-piperidinone | | 199.25 | 1.00 | 50.19 | 10.00 | |
| 2 | 623-73-4 | Ethyl diazoacetate | 1.085 | 114.1 | 1.05 | 52.70 | 6.01 | 5.54 |
| 3 | 109-72-8 | 1.6 M BuLi hexane | | | 1.60 | 80.30 | | 50.19 |
| 4 | 108-18-9 | Diisopropylamine | 0.720 | 101.19 | 1.60 | 80.30 | 8.13 | 11.29 |
| | 109-99-9 | THF on 4 molecular sieve | | | 10 vol. | | | 500 |
| 6 | 64-19-7 | 100% AcOH | 1.050 | 60.05 | 5.00 | 250.94 | 15.07 | 14.35 |

A freshly prepared solution of LDA (prepared by the dropwise addition, under An inert atmosphere at −78° C., of 50.19 ml of 1.6 M of BuLi in hexane to a Solution of 11.29 ml of diisopropylamine in 200 ml of dry THF) is added dropwise, under an inert atmosphere at −78° C., onto 10.0 g of N-Boc-piperidinone in suspension and 5.54 ml of ethyl diazoacetate in 300 ml of dry THF. The mixture is stirred at −78° C. for 4 hours and is then decomposed at −78° C. with 14.35 ml of concentrated AcOH. The mixture obtained is left at ambient temperature overnight, and the solvent is then evaporated off under reduced pressure, to 1/10 of its initial volume, diluted in diisopropyl ether, and washed 4 times with a saturated NaHCO$_3$ solution. The organic phase is dried over MgSO$_4$. The hydrated salt is removed by filtration and the dry filtrate is concentrated under reduced pressure so as to give 15.12 g of a viscous yellow oil. LC/MS: RT=2.84; [M+1]+=304.33. The product is used as it is for the subsequent step.

tert-Butyl 4-(diazoethoxycarbonylmethyl)-3,6-dihydro-2H-pyridine-1-carboxylate

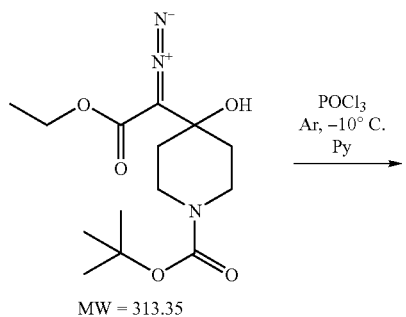

MW = 313.35

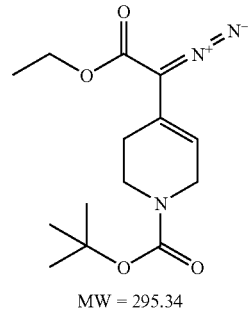

MW = 295.34

| CAS | Name | d | MM | eq | mmol | g | ml |
|---|---|---|---|---|---|---|---|
| 1 | P-31391-106-4 | | 313.35 | 1 | 48.25 | 15.12 | |
| 2 10025-87-3 | POCl$_3$ | 1.67 | 153.33 | 2 | 96.51 | 14.80 | 8.86 |
| 3 110-86-1 | Pyridine (4 Å m.s.) | 0.983 | 79.1 | 20 | 965.06 | 76.34 | 77.66 |
| 4 108-20-3 | iPr$_2$O | | | 5vol | | | 250 |
| 5 1310-73-2 | 0.1 M NaOH | | 40 | 1 | 48.25 | | 483 |

78.0 ml of dry pyridine are added to a solution of 15.12 g of tert-butyl 4-(diazoethoxycarbonylmethyl)-4-hydroxypiperidine-1-carboxylate into 250 ml of iPr₂O. The mixture is cooled to −10° C. and 8.86 ml of POCl₃ are added slowly with vigorous stirring. The mixture is then left to return to ambient temperature for 12 hours with stirring. The reaction mixture is decomposed with 500 ml of a 0.1 M NaOH solution, and is then extracted 3 times with EtOAc. The organic phase is washed with a saturated NaCl solution and dried over MgSO₄. The hydrated salt is removed by filtration and the dry filtrate is concentrated under reduced pressure to ¹/₁₀ of its initial volume. LC/MS: RT=4.57; [M+1]+=296.31 The product is used as it is for the subsequent step.

6-tert-Butyl 3-ethyl 2,4,5,7-tetrahydropyrazolo[3,4-c]pyridyl-3,6-dicarboxylate

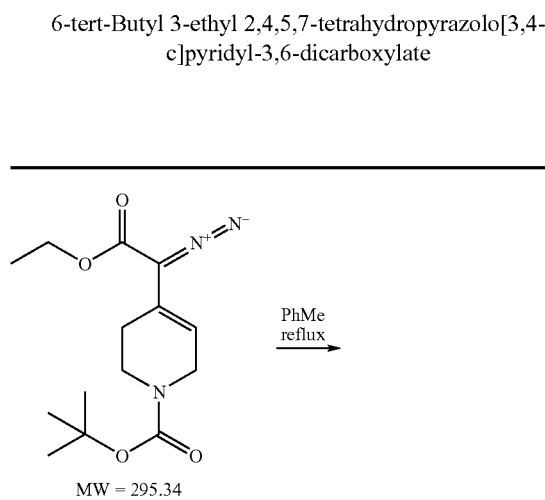

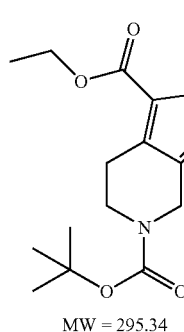

MW = 295.34

| | CAS | Name | d | MM | eq | mmol | mg | ml |
|---|---|---|---|---|---|---|---|---|
| 1 | | P-31391-120-4 | | 285.35 | 1.0 | 48.25 | | |
| 2 | 108-83-3 | PhMe | | | | | | 150 |

The solution of tert-butyl 4-(diazoethoxycarbonylmethyl)-3,6-dihydro-2H-pyridyl-1-carboxylate in Py/EtOAc obtained in the preceding step is added dropwise to 150 ml of toluene reflux. The azeotrope Py/PhMe is distilled at a rate equivalent to the rate of addition. One hour after the end of addition, the solution is left to cool to ambient temperature, the solvent is evaporated off under reduced pressure and the crude product obtained (15.05 g) is purified by flash chromatography (SiO₂, CH₂Cl₂/MeOH 1% NH₃ 7M$_{(MeOH)}$ 40:1 then 30:1 then 20:1). The solvent is evaporated off and 10.05 g (71% over 3 steps) of a black solid are obtained: LC/MS: RT=3.88; [M+1]+=296.27.

(tert-Butyl 2,4,5,7-tetrahydropyrazolo[3,4-c]pyridyl-6-carboxylate)-3-carboxylic acid

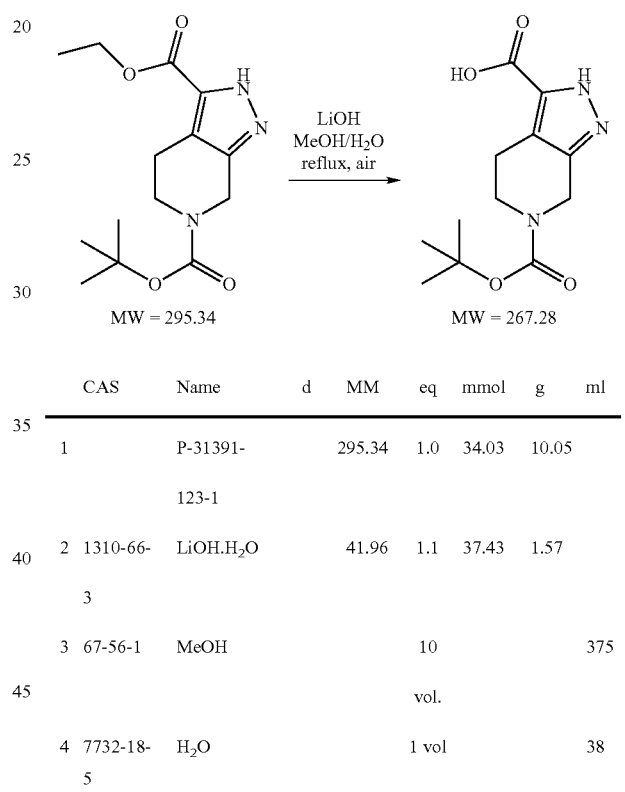

| | CAS | Name | d | MM | eq | mmol | g | ml |
|---|---|---|---|---|---|---|---|---|
| 1 | | P-31391-123-1 | | 295.34 | 1.0 | 34.03 | 10.05 | |
| 2 | 1310-66-3 | LiOH.H₂O | | 41.96 | 1.1 | 37.43 | 1.57 | |
| 3 | 67-56-1 | MeOH | | | 10 vol. | | | 375 |
| 4 | 7732-18-5 | H₂O | | | 1 vol | | | 38 |

1.57 g of LiOH and 38 ml of water are added to a solution of 10.05 g of 6-tert-butyl 3-ethyl 2,4,5,7-tetrahydropyrazolo[3,4-c]pyridyl-3,6-dicarboxylate in 375 ml of MeOH. The mixture obtained is refluxed overnight. The solution is cooled to ambient temperature and is then acidified to pH=2 with 50 ml of a 1M HCl solution. The solution is then extracted 4 times with EtOAc. The organic phase is washed with a saturated NaCl solution and then dried over Na₂SO₄. The salt obtained is removed by filtration and the solvent is evaporated off under reduced pressure so as to produce 8.90 g (98%) of a white solid. LC/MS: RT=3.21; [M+1]+=268.23.

Preparation of a Library of Products:

tert-Butyl 3-(alkylcarbamoyl, arylcarbamoyl, heteroarylcarbamoyl, etc.)-2,4,5,7-tetrahydropyrazolo[3,4-c]pyridine-6-carboxylate

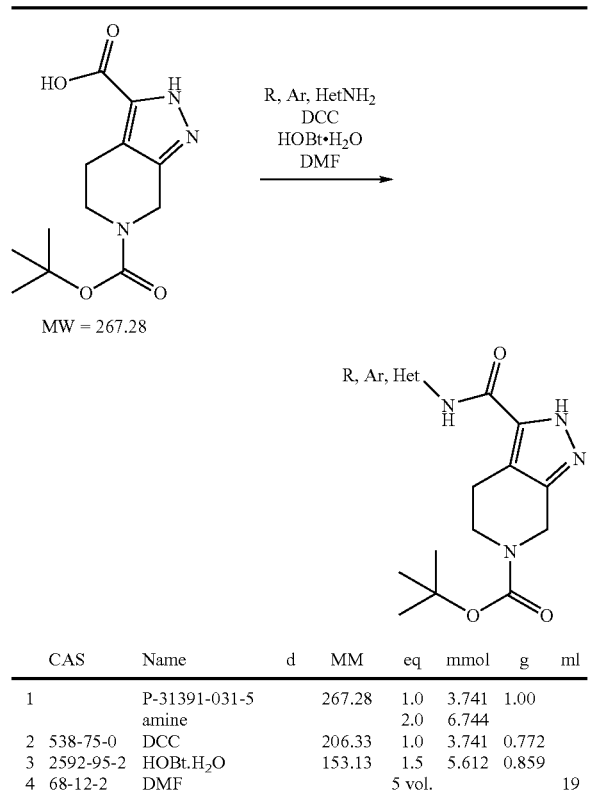

MW = 267.28

| CAS | Name | d | MM | eq | mmol | g | ml |
|---|---|---|---|---|---|---|---|
| 1 | P-31391-031-5 | | 267.28 | 1.0 | 3.741 | 1.00 | |
| | amine | | | 2.0 | 6.744 | | |
| 2 | 538-75-0 | DCC | | 206.33 | 1.0 | 3.741 | 0.772 | |
| 3 | 2592-95-2 | HOBt.H$_2$O | | 153.13 | 1.5 | 5.612 | 0.859 | |
| 4 | 68-12-2 | DMF | | | 5 vol. | | | 19 |

General Method:

DCC and HOBT.H$_2$O in solution in DMF with 2 eq of amine (R, Ar, or Het)-NH$_2$ are added to a solution of 1 eq of tert-butyl (2,4,5,7-tetrahydro-pyrazolo[3,4-c]pyridyl-6-carboxylate)-3-carboxylic acid in DMF and the mixture is stirred at ambient temperature for 3 h. The solvent is evaporated off under reduced pressure at 35° C. overnight. The crude product obtained is purified by flash chromatography (SiO$_2$, CH$_2$Cl$_2$/MeOH 1% NH$_3$ 7M$_{(MeOH)}$ 20:1 then 10:1 then 5:1, according to the products).

List of amines R1-NH$_2$ used (Table 1) [Comment: R1-NH$_2$=(R, Ar, or Het)-NH$_2$]:

TABLE 1

| Reference number of the amine | Structure |
|---|---|
| 1 | phenyl-NH$_2$ |
| 2 | benzyl-NH$_2$ |
| 3 | 2-methoxyphenyl-NH$_2$ |
| 4 | cyclohexyl-NH$_2$ |
| 5 | 2-(pyrrolidin-1-yl)ethyl-NH$_2$ |
| 6 | acetamidomethyl-NH$_2$ |
| 7 | piperidine (NH) |
| 8 | 3-morpholinopropyl-NH$_2$ |
| 9 | 2-chlorobenzyl-NH$_2$ |
| 10 | 4-fluorophenyl-NH$_2$ |
| 11 | furan-2-ylmethyl-NH$_2$ |
| 12 | pyridin-2-ylmethyl-NH$_2$ |
| 13 | 4-hydroxybutyl-NH$_2$ |
| 14 | ethyl 4-aminopiperidine-1-carboxylate |
| 15 | 1H-indazol-5-amine |

3-(Alkylcarbamoyl, arylcarbamoyl, heteroarylcarbamoyl, etc.)-4,5,6,7-tetrahydro-2H-pyrazolo[3,4-c]pyridin-6-ium trifluoroacetate

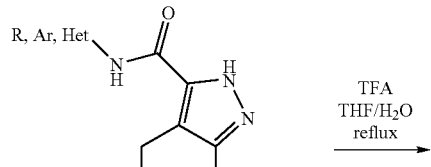

TFA
THF/H₂O
reflux

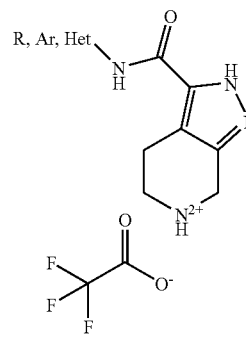

General Method:

16 eq of TFA are added to 1 eq of tert-butyl 3-(alkylcarbamoyl, arylcarbamoyl, heteroarylcarbamoyl, etc.)-2,4,5,7-tetrahydropyrazolo[3,4-c]pyridine-6-carboxylate in a 1:1 THF/water solution, and the solution is refluxed for 2 h. The solvent is evaporated off under reduced pressure and the viscous oil collected is dried under vacuum overnight. The product thus obtained is used without purification in the subsequent step.

6-(Alkyl, aryl, heteroaryl, etc.)carbonyl-4,5,6,7-tetrahydro-2H-pyrazolo[3,4-c]pyridine-3-(alkyl, aryl, hetyl, etc.)amide

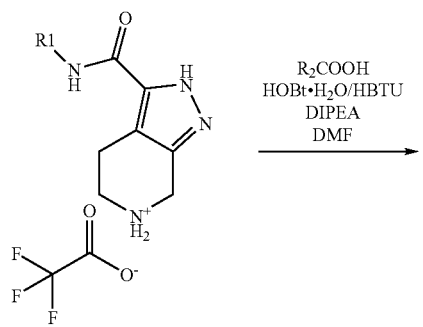

R₂COOH
HOBt·H₂O/HBTU
DIPEA
DMF

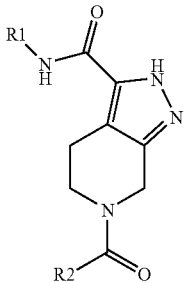

General Method:

A solution of 2.5M HOBt.H₂O (2 eq) in DMF, a solution of 0.833M HBTU in DMF (2 eq), a solution of 2.5M DIPEA (4 eq) in DMF and a suspension or a solution at an appropriate concentration of an R₂COOH (2 eq) in DMF are added, in order, to a solution of 1 eq of 3-(alkylcarbamoyl, arylcarbamoyl, heteroarylcarbamoyl, etc.)-4,5,6,7-tetrahydro-2H-pyrazolo[3,4-c]pyridin-6-ium trifluoroacetate in DMF. The solutions are stirred overnight at ambient temperature and are then acidified with 100 µl of 100% AcOH, filtered and purified by preparative LC/MS.

List of the acids R2COOH used (Table 2):

TABLE 2

| Reference number of the acid | Nomenclature |
| --- | --- |
| 1 | 1-Phenyl-1-cyclopropylcarboxylic acid |
| 2 | Acetic acid |
| 3 | Propiolic acid |
| 4 | Crotonic acid |
| 5 | Vinylacetic acid |
| 6 | Pyruvic acid |
| 7 | Sarcosine |
| 8 | Methoxyacetic acid |
| 9 | Lactic acid |
| 10 | 3,3-Dimethylacrylic acid |
| 11 | Cyclopropylacetic acid |
| 12 | Valeric acid |
| 13 | N,N-dimethylglycine |
| 14 | 3-Mercaptopropionic acid |
| 15 | (Methylthio)acetic acid |
| 16 | Pyrrole-2-carboxylic acid |
| 17 | 1-Cyanocyclopropanecarboxylic acid |
| 18 | 2-Furoic acid |
| 19 | 4-Pyrazolecarboxylic acid |
| 20 | Imidazole-4-carboxylic acid |
| 21 | 1-Cyclopentenecarboxylic acid |
| 22 | Acid |
| 23 | Acetoxyacetic acid |
| 24 | Hydantoic acid |
| 25 | Benzoic acid |
| 26 | Nicotinic acid |
| 27 | 2-Pyrazinecarboxylic acid |
| 28 | o-Toluic acid |
| 29 | Phenylacetic acid |
| 30 | Salicylic acid |
| 31 | 2-Fluorobenzoic acid |
| 32 | 3-Cyanobenzoic acid |
| 33 | 4-Vinylbenzoic acid |
| 34 | 2-Phenylpropionic acid |
| 35 | N-Methylanthranilic acid |
| 36 | 2-Methoxybenzoic acid |
| 37 | 2-Hydroxyphenylacetic acid |

TABLE 2-continued

| Reference number of the acid | Nomenclature |
|---|---|
| 38 | 4-Hydroxymethylbenzoic acid |
| 39 | 2-Fluorophenylbenzoic acid |
| 40 | 2,6-Difluorobenzoic acid |
| 41 | Indole-3-carboxylic acid |
| 42 | 3,5-Dimethylphenylacetic acid |
| 43 | 3-(Dimethylamino)benzoic acid |
| 44 | Piperonylic acid |
| 45 | DL-tropic acid |
| 46 | 3-Methoxyphenylacetic acid |
| 47 | 3-Methoxysalicylic acid |
| 48 | 4-(Methylthio)benzoic acid |
| 49 | 2-Chlorophenylacetic acid |
| 50 | 2-Naphthoic acid |
| 51 | 2-Chloro-6-fluorobenzoic acid |
| 52 | 1-Methylindole-3-carboxylic acid |
| 53 | 3-Acetamidobenzoic acid |
| 54 | 4-(Dimethylamino)salicylic acid |
| 55 | 2,3-Dimethoxybenzoic acid |
| 56 | 4-Chlorophenylpropionic acid |
| 57 | 2-Chloromandelic acid |
| 58 | 2-Chloro-6-fluorophenylacetic acid |
| 59 | 1-Phenyl-1-cyclopentanecarboxylic acid |
| 60 | 2,6-Dichlorobenzoic acid |
| 61 | 3-Methyl-2-phenylvaleric acid |
| 62 | 4-Phenylbenzoic acid |
| 63 | 2-Chloro-4-nitrobenzoic acid |
| 64 | 2-Benzylbenzoic acid |
| 65 | 2-Phenoxybenzoic acid |
| 66 | 2-Ethoxy-1-naphthoic acid |
| 67 | 4-(4-N-Propylphenyl)benzoic acid |
| 68 | 3,5-Dibromosalicylic acid |
| 69 | 2,6-Dichlorophenylacetic acid |
| 70 | Cyanoacetic acid |

Results

The following products are prepared according to the process described above.

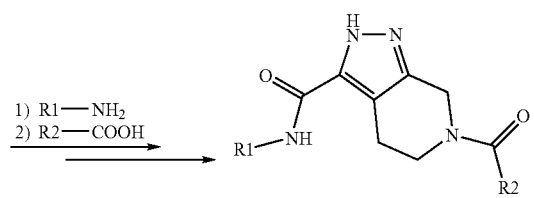

Scheme A

In order to simplify the representation of the products in Table 3 which follows, the pyrazolopiperidine ring presented in Scheme A is symbolized by the letter H, the amines R1-$NH_2$ which are linked to H are symbolized by the letter B followed by a number ranging from 1 to 15, corresponding to the products listed in Table 1, and the acids R2-COOH which are linked to H are symbolized by the letter A followed by a number from 1 to 70, corresponding to the products listed in Table 2.

Thus, a product referred to as A1-H—B1 corresponds to the following structure:

TABLE 3

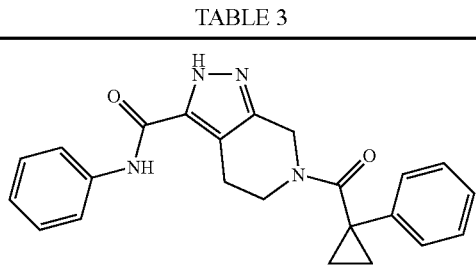

| A1-H-B1 | A2-H-B1 | A3-H-B1 | A4-H-B1 | A5-H-B1 | A6-H-B1 | A7-H-B1 |
|---|---|---|---|---|---|---|
| A1-H-B2 | A2-H-B2 | A3-H-B2 | A4-H-B2 | A5-H-B2 | A6-H-B2 | A7-H-B2 |
| A1-H-B3 | A2-H-B3 | A3-H-B3 | A4-H-B3 | A5-H-B3 | A6-H-B3 | A7-H-B3 |
| A1-H-B4 | A2-H-B4 | A3-H-B4 | A4-H-B4 | A5-H-B4 | A6-H-B4 | A7-H-B4 |
| A1-H-B5 | A2-H-B5 | A3-H-B5 | A4-H-B5 | A5-H-B5 | A6-H-B5 | A7-H-B5 |
| A1-H-B6 | A2-H-B6 | A3-H-B6 | A4-H-B6 | A5-H-B6 | A6-H-B6 | A7-H-B6 |
| A1-H-B7 | A2-H-B7 | A3-H-B7 | A4-H-B7 | A5-H-B7 | A6-H-B7 | A7-H-B7 |
| A1-H-B8 | A2-H-B8 | A3-H-B8 | A4-H-B8 | A5-H-B8 | A6-H-B8 | A7-H-B8 |
| A1-H-B9 | A2-H-B9 | A3-H-B9 | A4-H-B9 | A5-H-B9 | A6-H-B9 | A7-H-B9 |
| A1-H-B10 | A2-H-B10 | A3-H-B10 | A4-H-B10 | A5-H-B10 | A6-H-B10 | A7-H-B10 |
| A1-H-B11 | A2-H-B11 | A3-H-B11 | A4-H-B11 | A5-H-B11 | A6-H-B11 | A7-H-B11 |
| A1-H-B12 | A2-H-B12 | A3-H-B12 | A4-H-B12 | A5-H-B12 | A6-H-B12 | A7-H-B12 |
| A1-H-B13 | A2-H-B13 | A3-H-B13 | A4-H-B13 | A5-H-B13 | A6-H-B13 | A7-H-B13 |
| A1-H-B14 | A2-H-B14 | A3-H-B14 | A4-H-B14 | A5-H-B14 | A6-H-B14 | A7-H-B14 |
| A1-H-B15 | A2-H-B15 | A3-H-B15 | A4-H-B15 | A5-H-B15 | A6-H-B15 | A7-H-B15 |
| A8-H-B1 | A9-H-B1 | A10-H-B1 | A11-H-B1 | A12-H-B1 | A13-H-B1 | A14-H-B1 |
| A8-H-B2 | A9-H-B2 | A10-H-B2 | A11-H-B2 | A12-H-B2 | A13-H-B2 | A14-H-B2 |
| A8-H-B3 | A9-H-B3 | A10-H-B3 | A11-H-B3 | A12-H-B3 | A13-H-B3 | A14-H-B3 |
| A8-H-B4 | A9-H-B4 | A10-H-B4 | A11-H-B4 | A12-H-B4 | A13-H-B4 | A14-H-B4 |
| A8-H-B5 | A9-H-B5 | A10-H-B5 | A11-H-B5 | A12-H-B5 | A13-H-B5 | A14-H-B5 |
| A8-H-B6 | A9-H-B6 | A10-H-B6 | A11-H-B6 | A12-H-B6 | A13-H-B6 | A14-H-B6 |
| A8-H-B7 | A9-H-B7 | A10-H-B7 | A11-H-B7 | A12-H-B7 | A13-H-B7 | A14-H-B7 |
| A8-H-B8 | A9-H-B8 | A10-H-B8 | A11-H-B8 | A12-H-B8 | A13-H-B8 | A14-H-B8 |
| A8-H-B9 | A9-H-B9 | A10-H-B9 | A11-H-B9 | A12-H-B9 | A13-H-B9 | A14-H-B9 |
| A8-H-B10 | A9-H-B10 | A10-H-B10 | A11-H-B10 | A12-H-B10 | A13-H-B10 | A14-H-B10 |

TABLE 3-continued

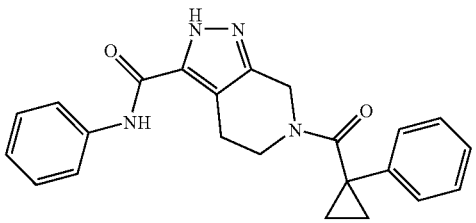

| A8-H-B11 | A9-H-B11 | A10-H-B11 | A11-H-B11 | A12-H-B11 | A13-H-B11 | A14-H-B11 |
| --- | --- | --- | --- | --- | --- | --- |
| A8-H-B12 | A9-H-B12 | A10-H-B12 | A11-H-B12 | A12-H-B12 | A13-H-B12 | A14-H-B12 |
| A8-H-B13 | A9-H-B13 | A10-H-B13 | A11-H-B13 | A12-H-B13 | A13-H-B13 | A14-H-B13 |
| A8-H-B14 | A9-H-B14 | A10-H-B14 | A11-H-B14 | A12-H-B14 | A13-H-B14 | A14-H-B14 |
| A8-H-B15 | A9-H-B15 | A10-H-B15 | A11-H-B15 | A12-H-B15 | A13-H-B15 | A14-H-B15 |
| A15-H-B1 | A16-H-B1 | A17-H-B1 | A18-H-B1 | A19-H-B1 | A20-H-B1 | A21-H-B1 |
| A15-H-B2 | A16-H-B2 | A17-H-B2 | A18-H-B2 | A19-H-B2 | A20-H-B2 | A21-H-B2 |
| A15-H-B3 | A16-H-B3 | A17-H-B3 | A18-H-B3 | A19-H-B3 | A20-H-B3 | A21-H-B3 |
| A15-H-B4 | A16-H-B4 | A17-H-B4 | A18-H-B4 | A19-H-B4 | A20-H-B4 | A21-H-B4 |
| A15-H-B5 | A16-H-B5 | A17-H-B5 | A18-H-B5 | A19-H-B5 | A20-H-B5 | A21-H-B5 |
| A15-H-B6 | A16-H-B6 | A17-H-B6 | A18-H-B6 | A19-H-B6 | A20-H-B6 | A21-H-B6 |
| A15-H-B7 | A16-H-B7 | A17-H-B7 | A18-H-B7 | A19-H-B7 | A20-H-B7 | A21-H-B7 |
| A15-H-B8 | A16-H-B8 | A17-H-B8 | A18-H-B8 | A19-H-B8 | A20-H-B8 | A21-H-B8 |
| A15-H-B9 | A16-H-B9 | A17-H-B9 | A18-H-B9 | A19-H-B9 | A20-H-B9 | A21-H-B9 |
| A15-H-B10 | A16-H-B10 | A17-H-B10 | A18-H-B10 | A19-H-B10 | A20-H-B10 | A21-H-B10 |
| A15-H-B11 | A16-H-B11 | A17-H-B11 | A18-H-B11 | A19-H-B11 | A20-H-B11 | A21-H-B11 |
| A15-H-B12 | A16-H-B12 | A17-H-B12 | A18-H-B12 | A19-H-B12 | A20-H-B12 | A21-H-B12 |
| A15-H-B13 | A16-H-B13 | A17-H-B13 | A18-H-B13 | A19-H-B13 | A20-H-B13 | A21-H-B13 |
| A15-H-B14 | A16-H-B14 | A17-H-B14 | A18-H-B14 | A19-H-B14 | A20-H-B14 | A21-H-B14 |
| A15-H-B15 | A16-H-B15 | A17-H-B15 | A18-H-B15 | A19-H-B15 | A20-H-B15 | A21-H-B15 |
| A22-H-B1 | A23-H-B1 | A24-H-B1 | A25-H-B1 | A26-H-B1 | A27-H-B1 | A28-H-B1 |
| A22-H-B2 | A23-H-B2 | A24-H-B2 | A25-H-B2 | A26-H-B2 | A27-H-B2 | A28-H-B2 |
| A22-H-B3 | A23-H-B3 | A24-H-B3 | A25-H-B3 | A26-H-B3 | A27-H-B3 | A28-H-B3 |
| A22-H-B4 | A23-H-B4 | A24-H-B4 | A25-H-B4 | A26-H-B4 | A27-H-B4 | A28-H-B4 |
| A22-H-B5 | A23-H-B5 | A24-H-B5 | A25-H-B5 | A26-H-B5 | A27-H-B5 | A28-H-B5 |
| A22-H-B6 | A23-H-B6 | A24-H-B6 | A25-H-B6 | A26-H-B6 | A27-H-B6 | A28-H-B6 |
| A22-H-B7 | A23-H-B7 | A24-H-B7 | A25-H-B7 | A26-H-B7 | A27-H-B7 | A28-H-B7 |
| A22-H-B8 | A23-H-B8 | A24-H-B8 | A25-H-B8 | A26-H-B8 | A27-H-B8 | A28-H-B8 |
| A22-H-B9 | A23-H-B9 | A24-H-B9 | A25-H-B9 | A26-H-B9 | A27-H-B9 | A28-H-B9 |
| A22-H-B10 | A23-H-B10 | A24-H-B10 | A25-H-B10 | A26-H-B10 | A27-H-B10 | A28-H-B10 |
| A22-H-B11 | A23-H-B11 | A24-H-B11 | A25-H-B11 | A26-H-B11 | A27-H-B11 | A28-H-B11 |
| A22-H-B12 | A23-H-B12 | A24-H-B12 | A25-H-B12 | A26-H-B12 | A27-H-B12 | A28-H-B12 |
| A22-H-B13 | A23-H-B13 | A24-H-B13 | A25-H-B13 | A26-H-B13 | A27-H-B13 | A28-H-B13 |
| A22-H-B14 | A23-H-B14 | A24-H-B14 | A25-H-B14 | A26-H-B14 | A27-H-B14 | A28-H-B14 |
| A22-H-B15 | A23-H-B15 | A24-H-B15 | A25-H-B15 | A26-H-B15 | A27-H-B15 | A28-H-B15 |
| A29-H-B1 | A30-H-B1 | A31-H-B1 | A32-H-B1 | A33-H-B1 | A34-H-B1 | A35-H-B1 |
| A29-H-B2 | A30-H-B2 | A31-H-B2 | A32-H-B2 | A33-H-B2 | A34-H-B2 | A35-H-B2 |
| A29-H-B3 | A30-H-B3 | A31-H-B3 | A32-H-B3 | A33-H-B3 | A34-H-B3 | A35-H-B3 |
| A29-H-B4 | A30-H-B4 | A31-H-B4 | A32-H-B4 | A33-H-B4 | A34-H-B4 | A35-H-B4 |
| A29-H-B5 | A30-H-B5 | A31-H-B5 | A32-H-B5 | A33-H-B5 | A34-H-B5 | A35-H-B5 |
| A29-H-B6 | A30-H-B6 | A31-H-B6 | A32-H-B6 | A33-H-B6 | A34-H-B6 | A35-H-B6 |
| A29-H-B7 | A30-H-B7 | A31-H-B7 | A32-H-B7 | A33-H-B7 | A34-H-B7 | A35-H-B7 |
| A29-H-B8 | A30-H-B8 | A31-H-B8 | A32-H-B8 | A33-H-B8 | A34-H-B8 | A35-H-B8 |
| A29-H-B9 | A30-H-B9 | A31-H-B9 | A32-H-B9 | A33-H-B9 | A34-H-B9 | A35-H-B9 |
| A29-H-B10 | A30-H-B10 | A31-H-B10 | A32-H-B10 | A33-H-B10 | A34-H-B10 | A35-H-B10 |
| A29-H-B11 | A30-H-B11 | A31-H-B11 | A32-H-B11 | A33-H-B11 | A34-H-B11 | A35-H-B11 |
| A29-H-B12 | A30-H-B12 | A31-H-B12 | A32-H-B12 | A33-H-B12 | A34-H-B12 | A35-H-B12 |
| A29-H-B13 | A30-H-B13 | A31-H-B13 | A32-H-B13 | A33-H-B13 | A34-H-B13 | A35-H-B13 |
| A29-H-B14 | A30-H-B14 | A31-H-B14 | A32-H-B14 | A33-H-B14 | A34-H-B14 | A35-H-B14 |
| A29-H-B15 | A30-H-B15 | A31-H-B15 | A32-H-B15 | A33-H-B15 | A34-H-B15 | A35-H-B15 |
| A36-H-B1 | A37-H-B1 | A38-H-B1 | A39-H-B1 | A40-H-B1 | A41-H-B1 | A42-H-B1 |
| A36-H-B2 | A37-H-B2 | A38-H-B2 | A39-H-B2 | A40-H-B2 | A41-H-B2 | A42-H-B2 |
| A36-H-B3 | A37-H-B3 | A38-H-B3 | A39-H-B3 | A40-H-B3 | A41-H-B3 | A42-H-B3 |
| A36-H-B4 | A37-H-B4 | A38-H-B4 | A39-H-B4 | A40-H-B4 | A41-H-B4 | A42-H-B4 |
| A36-H-B5 | A37-H-B5 | A38-H-B5 | A39-H-B5 | A40-H-B5 | A41-H-B5 | A42-H-B5 |
| A36-H-B6 | A37-H-B6 | A38-H-B6 | A39-H-B6 | A40-H-B6 | A41-H-B6 | A42-H-B6 |
| A36-H-B7 | A37-H-B7 | A38-H-B7 | A39-H-B7 | A40-H-B7 | A41-H-B7 | A42-H-B7 |
| A36-H-B8 | A37-H-B8 | A38-H-B8 | A39-H-B8 | A40-H-B8 | A41-H-B8 | A42-H-B8 |
| A36-H-B9 | A37-H-B9 | A38-H-B9 | A39-H-B9 | A40-H-B9 | A41-H-B9 | A42-H-B9 |
| A36-H-B10 | A37-H-B10 | A38-H-B10 | A39-H-B10 | A40-H-B10 | A41-H-B10 | A42-H-B10 |
| A36-H-B11 | A37-H-B11 | A38-H-B11 | A39-H-B11 | A40-H-B11 | A41-H-B11 | A42-H-B11 |
| A36-H-B12 | A37-H-B12 | A38-H-B12 | A39-H-B12 | A40-H-B12 | A41-H-B12 | A42-H-B12 |
| A36-H-B13 | A37-H-B13 | A38-H-B13 | A39-H-B13 | A40-H-B13 | A41-H-B13 | A42-H-B13 |
| A36-H-B14 | A37-H-B14 | A38-H-B14 | A39-H-B14 | A40-H-B14 | A41-H-B14 | A42-H-B14 |
| A36-H-B15 | A37-H-B15 | A38-H-B15 | A39-H-B15 | A40-H-B15 | A41-H-B15 | A42-H-B15 |
| A43-H-B1 | A44-H-B1 | A45-H-B1 | A46-H-B1 | A47-H-B1 | A48-H-B1 | A49-H-B1 |
| A43-H-B2 | A44-H-B2 | A45-H-B2 | A46-H-B2 | A47-H-B2 | A48-H-B2 | A49-H-B2 |

TABLE 3-continued

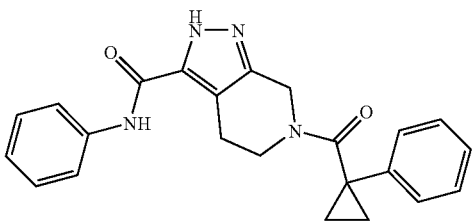

| | | | | | | |
|---|---|---|---|---|---|---|
| A43-H-B3 | A44-H-B3 | A45-H-B3 | A46-H-B3 | A47-H-B3 | A48-H-B3 | A49-H-B3 |
| A43-H-B4 | A44-H-B4 | A45-H-B4 | A46-H-B4 | A47-H-B4 | A48-H-B4 | A49-H-B4 |
| A43-H-B5 | A44-H-B5 | A45-H-B5 | A46-H-B5 | A47-H-B5 | A48-H-B5 | A49-H-B5 |
| A43-H-B6 | A44-H-B6 | A45-H-B6 | A46-H-B6 | A47-H-B6 | A48-H-B6 | A49-H-B6 |
| A43-H-B7 | A44-H-B7 | A45-H-B7 | A46-H-B7 | A47-H-B7 | A48-H-B7 | A49-H-B7 |
| A43-H-B8 | A44-H-B8 | A45-H-B8 | A46-H-B8 | A47-H-B8 | A48-H-B8 | A49-H-B8 |
| A43-H-B9 | A44-H-B9 | A45-H-B9 | A46-H-B9 | A47-H-B9 | A48-H-B9 | A49-H-B9 |
| A43-H-B10 | A44-H-B10 | A45-H-B10 | A46-H-B10 | A47-H-B10 | A48-H-B10 | A49-H-B10 |
| A43-H-B11 | A44-H-B11 | A45-H-B11 | A46-H-B11 | A47-H-B11 | A48-H-B11 | A49-H-B11 |
| A43-H-B12 | A44-H-B12 | A45-H-B12 | A46-H-B12 | A47-H-B12 | A48-H-B12 | A49-H-B12 |
| A43-H-B13 | A44-H-B13 | A45-H-B13 | A46-H-B13 | A47-H-B13 | A48-H-B13 | A49-H-B13 |
| A43-H-B14 | A44-H-B14 | A45-H-B14 | A46-H-B14 | A47-H-B14 | A48-H-B14 | A49-H-B14 |
| A50-H-B1 | A51-H-B1 | A52-H-B1 | A53-H-B1 | A54-H-B1 | A55-H-B1 | A56-H-B1 |
| A50-H-B2 | A51-H-B2 | A52-H-B2 | A53-H-B2 | A54-H-B2 | A55-H-B2 | A56-H-B2 |
| A50-H-B3 | A51-H-B3 | A52-H-B3 | A53-H-B3 | A54-H-B3 | A55-H-B3 | A56-H-B3 |
| A50-H-B4 | A51-H-B4 | A52-H-B4 | A53-H-B4 | A54-H-B4 | A55-H-B4 | A56-H-B4 |
| A50-H-B5 | A51-H-B5 | A52-H-B5 | A53-H-B5 | A54-H-B5 | A55-H-B5 | A56-H-B5 |
| A50-H-B6 | A51-H-B6 | A52-H-B6 | A53-H-B6 | A54-H-B6 | A55-H-B6 | A56-H-B6 |
| A50-H-B7 | A51-H-B7 | A52-H-B7 | A53-H-B7 | A54-H-B7 | A55-H-B7 | A56-H-B7 |
| A50-H-B8 | A51-H-B8 | A52-H-B8 | A53-H-B8 | A54-H-B8 | A55-H-B8 | A56-H-B8 |
| A50-H-B9 | A51-H-B9 | A52-H-B9 | A53-H-B9 | A54-H-B9 | A55-H-B9 | A56-H-B9 |
| A50-H-B10 | A51-H-B10 | A52-H-B10 | A53-H-B10 | A54-H-B10 | A55-H-B10 | A56-H-B10 |
| A50-H-B11 | A51-H-B11 | A52-H-B11 | A53-H-B11 | A54-H-B11 | A55-H-B11 | A56-H-B11 |
| A50-H-B12 | A51-H-B12 | A52-H-B12 | A53-H-B12 | A54-H-B12 | A55-H-B12 | A56-H-B12 |
| A50-H-B13 | A51-H-B13 | A52-H-B13 | A53-H-B13 | A54-H-B13 | A55-H-B13 | A56-H-B13 |
| A50-H-B14 | A51-H-B14 | A52-H-B14 | A53-H-B14 | A54-H-B14 | A55-H-B14 | A56-H-B14 |
| A50-H-B15 | A51-H-B15 | A52-H-B15 | A53-H-B15 | A54-H-B15 | A55-H-B15 | A56-H-B15 |
| A57-H-B1 | A58-H-B1 | A59-H-B1 | A60-H-B1 | A61-H-B1 | A62-H-B1 | A63-H-B1 |
| A57-H-B2 | A58-H-B2 | A59-H-B2 | A60-H-B2 | A61-H-B2 | A62-H-B2 | A63-H-B2 |
| A57-H-B3 | A58-H-B3 | A59-H-B3 | A60-H-B3 | A61-H-B3 | A62-H-B3 | A63-H-B3 |
| A57-H-B4 | A58-H-B4 | A59-H-B4 | A60-H-B4 | A61-H-B4 | A62-H-B4 | A63-H-B4 |
| A57-H-B5 | A58-H-B5 | A59-H-B5 | A60-H-B5 | A61-H-B5 | A62-H-B5 | A63-H-B5 |
| A57-H-B6 | A58-H-B6 | A59-H-B6 | A60-H-B6 | A61-H-B6 | A62-H-B6 | A63-H-B6 |
| A57-H-B7 | A58-H-B7 | A59-H-B7 | A60-H-B7 | A61-H-B7 | A62-H-B7 | A63-H-B7 |
| A57-H-B8 | A58-H-B8 | A59-H-B8 | A60-H-B8 | A61-H-B8 | A62-H-B8 | A63-H-B8 |
| A57-H-B9 | A58-H-B9 | A59-H-B9 | A60-H-B9 | A61-H-B9 | A62-H-B9 | A63-H-B9 |
| A57-H-B10 | A58-H-B10 | A59-H-B10 | A60-H-B10 | A61-H-B10 | A62-H-B10 | A63-H-B10 |
| A57-H-B11 | A58-H-B11 | A59-H-B11 | A60-H-B11 | A61-H-B11 | A62-H-B11 | A63-H-B11 |
| A57-H-B12 | A58-H-B12 | A59-H-B12 | A60-H-B12 | A61-H-B12 | A62-H-B12 | A63-H-B12 |
| A57-H-B13 | A58-H-B13 | A59-H-B13 | A60-H-B13 | A61-H-B13 | A62-H-B13 | A63-H-B13 |
| A57-H-B14 | A58-H-B14 | A59-H-B14 | A60-H-B14 | A61-H-B14 | A62-H-B14 | A63-H-B14 |
| A57-H-B15 | A58-H-B15 | A59-H-B15 | A60-H-B15 | A61-H-B15 | A62-H-B15 | A63-H-B15 |
| A64-H-B1 | A65-H-B1 | A66-H-B1 | A67-H-B1 | A68-H-B1 | A69-H-B1 | A70-H-B1 |
| A64-H-B2 | A65-H-B2 | A66-H-B2 | A67-H-B2 | A68-H-B2 | A69-H-B2 | A70-H-B2 |
| A64-H-B3 | A65-H-B3 | A66-H-B3 | A67-H-B3 | A68-H-B3 | A69-H-B3 | A70-H-B3 |
| A64-H-B4 | A65-H-B4 | A66-H-B4 | A67-H-B4 | A68-H-B4 | A69-H-B4 | A70-H-B4 |
| A64-H-B5 | A65-H-B5 | A66-H-B5 | A67-H-B5 | A68-H-B5 | A69-H-B5 | A70-H-B5 |
| A64-H-B6 | A65-H-B6 | A66-H-B6 | A67-H-B6 | A68-H-B6 | A69-H-B6 | A70-H-B6 |
| A64-H-B7 | A65-H-B7 | A66-H-B7 | A67-H-B7 | A68-H-B7 | A69-H-B7 | A70-H-B7 |
| A64-H-B8 | A65-H-B8 | A66-H-B8 | A67-H-B8 | A68-H-B8 | A69-H-B8 | A70-H-B8 |
| A64-H-B9 | A65-H-B9 | A66-H-B9 | A67-H-B9 | A68-H-B9 | A69-H-B9 | A70-H-B9 |
| A64-H-B10 | A65-H-B10 | A66-H-B10 | A67-H-B10 | A68-H-B10 | A69-H-B10 | A70-H-B10 |
| A64-H-B11 | A65-H-B11 | A66-H-B11 | A67-H-B11 | A68-H-B11 | A69-H-B11 | A70-H-B11 |
| A64-H-B12 | A65-H-B12 | A66-H-B12 | A67-H-B12 | A68-H-B12 | A69-H-B12 | A70-H-B12 |
| A64-H-B13 | A65-H-B13 | A66-H-B13 | A67-H-B13 | A68-H-B13 | A69-H-B13 | A70-H-B13 |
| A64-H-B14 | A65-H-B14 | A66-H-B14 | A67-H-B14 | A68-H-B14 | A69-H-B14 | A70-H-B14 |
| A64-H-B15 | A65-H-B15 | A66-H-B15 | A67-H-B15 | A68-H-B15 | A69-H-B15 | A70-H-B15 |

EXAMPLE 1
3-(5,6-Dimethyl-1H-benzoimidazol-2-yl)-2,4,5,7-tetrahydro-pyrazolo[3,4-c]pyridine-6-carboxylic acid 2-phenylethylamide

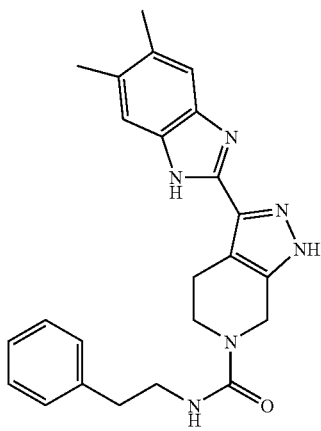

3-(5,6-Dimethyl-1H-benzoimidazol-2-yl)-2,4,5,7-tetrahydropyrazolo-[3,4-c]pyridine-6-carboxylic acid 2-phenylethylamide can be prepared in the following way:

10 mg of 3-(5,6-dimethyl-1H-benzimidazol-2-yl)-4,5,6,7-tetrahydro-2H-pyrazolo[3,4-c]pyridine are suspended in 0.3 ml of tetrahydrofuran. 7.8 µl of 2-phenylethyl isocyanate are added and the reaction mixture is stirred at ambient temperature for 20 hours and then concentrated under reduced pressure.

The evaporation residue is purified by LC/MS (method B). After purification by LC/MS, the fractions containing the 3-(5,6-Dimethyl-1H-benzoimidazol-2-yl)-2,4,5,7-tetrahydropyrazolo[3,4-c]pyridine-6-carboxylic acid 2-phenylethylamide are combined and loaded onto SCX phase (500 mg of CUBCX1-HL phase). The SCX phase is subsequently washed with methanol and then extracted with a solution of 2M ammonia in methanol. The extraction solution obtained is then concentrated under reduced pressure. 1.2 mg of 3-(5,6-dimethyl-1H-benzoimidazol-2-yl)-2,4,5,7-tetrahydropyrazolo[3,4-c]-pyridine-6-carboxylic acid 2-phenylethylamide are thus obtained in the form of a white powder, the characteristics of which are as follows:

LC/MS (method A): molecular ion detected: 415.29; retention time=3.48 minutes

EXAMPLE 2
3-(5,6-Dimethyl-1H-benzoimidazol-2-yl)-6-methanesulphonyl-4,5,6,7-tetrahydro-2H-pyrazolo[3,4-c]pyridine

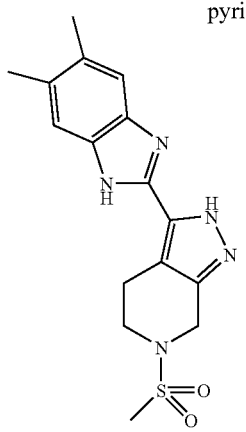

3-(5,6-Dimethyl-1H-benzoimidazol-2-yl)-6-methanesulphonyl-4,5,6,7-tetrahydro-2H-pyrazolo[3,4-c]pyridine can be prepared in the following way:

10 mg of 3-(5,6-dimethyl-1H-benzimidazol-2-yl)-4,5,6,7-tetrahydro-2H-pyrazolo[3,4-c]pyridine are suspended in 0.3 ml of dichloromethane. 15.8 µl of triethylamine are added, along with 4.5 µl of methanesulphonyl chloride. The reaction mixture is stirred at ambient temperature for 20 hours and is then concentrated under reduced pressure.

The evaporation residue is purified by LC/MS (method B). After purification by LC/MS, the fractions containing 3-(5,6-dimethyl-1H-benzoimidazol-2-yl)-6-methanesulphonyl-4,5,6,7-tetrahydro-2H-pyrazolo[3,4-c]pyridine are combined and loaded onto SCX phase (500 mg of CUBCX1-HL phase). The SCX phase is subsequently washed with methanol and then extracted with a solution of 2M ammonia in methanol. The extraction solution obtained is then concentrated under reduced pressure. 4.2 mg of 3-(5,6-dimethyl-1H-benzoimidazol-2-yl)-6-methanesulphonyl-4,5,6,7-tetrahydro-2H-pyrazolo-[3,4-c]pyridine are thus obtained in the form of a white powder, the characteristics of which are as follows:

LC/MS (method A): molecular ion detected: 346.30; retention time=3.08 minutes.

$^1$H NMR (300 MHz, (CD$_3$)$_2$SO, δ in ppm): 2.32 (broad s: 6H); 3.02 (s: 3H); 3.03 (mt: 2H); 3.52 (broad t, J=5 Hz: 2H); 4.45 (broad s: 2H); 7.24 (broad s: 1H); 7.42 (broad s: 1H); 12.45 (unresolved peak: 1H); 13.07 (unresolved peak: 1H).

EXAMPLE 3
[3-(5,6-Dimethyl-1H-benzoimidazol-2-yl)-2,4,5,7-tetrahydro-pyrazolo[3,4-c]pyridin-6-yl]-3-pyridinylmethanone

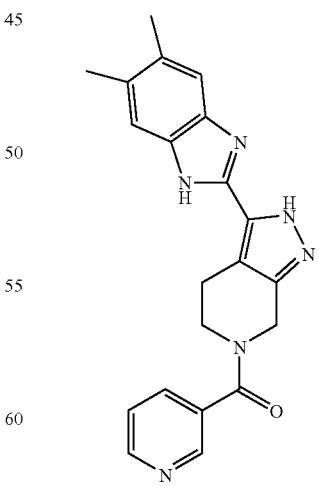

[3-(5,6-Dimethyl-1H-benzoimidazol-2-yl)-2,4,5,7-tetrahydropyrazolo-[3,4-c]pyridin-6-yl]-3-pyridinylmethanone can be prepared in the following way:

10 mg of 3-(5,6-dimethyl-1H-benzimidazol-2-yl)-4,5,6,7-tetrahydro-2H-pyrazolo[3,4-c]pyridine are suspended in 0.3 ml of DMF. 6.9 mg of nicotinic acid are added, followed by 7.6 mg of HOBT and 8.7 μl of diisopropylcarbodiimide. The reaction mixture is stirred at ambient temperature for 20 hours and is then concentrated under reduced pressure.

The evaporation residue is purified by LC/MS (method B). After purification by LC/MS, the fractions containing the [3-(5,6-dimethyl-1H-benzoimidazol-2-yl)-2,4,5,7-tetrahydropyrazolo[3,4-c]pyridin-6-yl]-3-pyridinylmethanone are combined and loaded onto SCX phase (500 mg of CUBCX1-HL phase). The SCX phase is subsequently washed with methanol and then extracted with a solution of 2M ammonia in methanol. The extraction solution obtained is then concentrated under reduced pressure. 5.3 mg of [3-(5,6-dimethyl-1H-benzoimidazol-2-yl)-2,4,5,7-tetrahydropyrazolo[3,4-c]pyridin-6-yl]-3-pyridinyl-methanone are thus obtained in the form of a white powder, the characteristics of which are as follows:

LC/MS (method A): molecular ion detected: 373.31; retention time=2.87 minutes $^1$H NMR (400 MHz, (CD$_3$)$_2$SO, at a temperature of 373K, δ in ppm): 2.35 (s: 6H); from 2.90 to 3.10 (mt: 2H); 3.76 (unresolved peak: 2H); 4.76 (broad s: 2H); 7.27 (unresolved peak: 1H); 7.40 (unresolved peak: 1H); 7.51 (dd, J=8 and 5 Hz: 1H); 7.90 (broad d, J=8 Hz: 1H); 8.70 (mt: 2H); from 11.80 to 12.20 (broad unresolved peak: 1H); from 12.50 to 13.00 (broad unresolved peak: 1H).

EXAMPLE 4

6-(3-Chlorobenzyl)-3-(5,6-dimethyl-1H-benzoimidazol-2-yl)-4,5,6,7-tetrahydro-2H-pyrazolo[3,4-c]pyridine

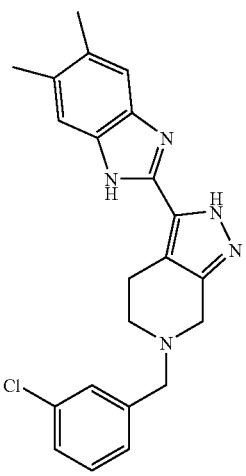

6-(3-Chlorobenzyl)-3-(5,6-dimethyl-1H-benzoimidazol-2-yl)-4,5,6,7-tetrahydro-2H-pyrazolo[3,4-c]pyridine can be prepared in the following way: 10 mg of 3-(5,6-dimethyl-1H-benzoimidazol-2-yl)-4,5,6,7-tetrahydro-2H-pyrazolo[3,4-c]pyridine are suspended in 0.3 ml of methanol. 12.7 μl of 3-chlorobenzaldehyde are added, followed by 4.7 mg of NaBH$_3$CN. The reaction mixture is stirred at ambient temperature for 20 hours and is then concentrated under reduced pressure.

The evaporation residue is purified by LC/MS (method B). After purification by LC/MS, the fractions containing the 6-(3-chlorobenzyl)-3-(5,6-dimethyl-1H-benzoimidazol-2-yl)-4,5,6,7-tetrahydro-2H-pyrazolo[3,4-c]pyridine are combined and loaded onto a SCX phase (500 mg of CUBCX1-HL phase). The SCX phase is subsequently washed with methanol and then extracted with a solution of 2M ammonia in methanol. The extraction solution obtained is then concentrated under reduced pressure. 4 mg of 6-(3-chlorobenzyl)-3-(5,6-dimethyl-1H-benzoimidazol-2-yl)-4,5,6,7-tetrahydro-2H-pyrazolo-[3,4-c]pyridine are thus obtained in the form of a white powder, the characteristics of which are as follows:

LC/MS (method A): molecular ion detected: 392.26; retention time 3.18 minutes.

$^1$H NMR (400 MHz, (CD$_3$)$_2$SO, at a temperature of 373K, δ in ppm): 2.35 and 2.36 (2 s: 6H in total); 2.83 (t, J=5.5 Hz: 2H); from 2.90 to 3.00 (mt: 2H); 3.62 (broad s: 2H); 3.78 (s: 2H); from 7.25 to 7.50 (mt: 6H); 11.91 (unresolved peak: 1H); from 12.30 to 12.60 (broad unresolved peak: 1H).

EXAMPLE 5

[3-(1H-Benzoimidazol-2-yl)-2,4,5,7-tetrahydropyrazolo[3,4-c]-pyridin-6-yl]-3-pyridinylmethanone

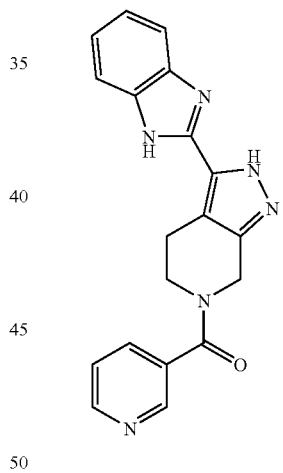

[3-(1H-Benzoimidazol-2-yl)-2,4,5,7-tetrahydropyrazolo[3,4-c]pyridin-6-yl]-3-pyridinylmethanone can be prepared in the following way:

15 mg of 3-(1H-benzimidazol-2-yl)-4,5,6,7-tetrahydro-2H-pyrazolo[3,4-c]-pyridine hydrochloride are suspended in 0.5 ml of DMF. 24.3 mg of diisopropylethylamine are added, followed by 12.7 mg of HOBT, 11.9 mg of diisopropylcarbodiimide and 11.6 mg of nicotinic acid. The reaction mixture is stirred at ambient temperature for 20 hours and then concentrated under reduced pressure.

The evaporation residue is purified by LC/MS (method B). After purification by LC/MS, the fractions containing the [3-(1H-benzoimidazol-2-yl)-2,4,5,7-tetrahydropyrazolo[3,4-c]pyridin-6-yl]-3-pyridinylmethanone are combined and loaded onto SCX phase (500 mg of CUBCX1-HL phase). The SCX phase is subsequently washed with methanol and then extracted with a solution of 2M ammonia in methanol. The extraction solution obtained is then concentrated under reduced pressure. 7.7 mg of [3-(1H-benzoimidazol-2-yl)-2,4,5,7-tetrahydropyrazolo[3,4-c]pyridin-6-yl]-3-pyridinyl-methanone are thus obtained in the form of a white powder, the characteristics of which are as follows:

LC/MS (method A): molecular ion detected: 345.22; retention time=1.95 minutes

EXAMPLE 6

6-(3-Chlorobenzyl)-3-(1H-benzoimidazol-2-yl)-4,5,6,7-tetrahydro-2H-pyrazolo[3,4-c]pyridine

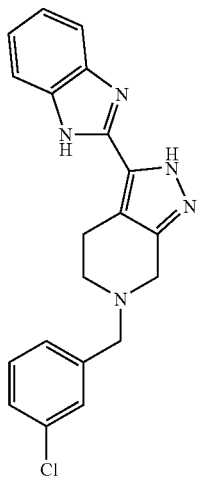

6-(3-Chlorobenzyl)-3-(1H-benzoimidazol-2-yl)-4,5, 6,7-tetrahydro-2H-pyrazolo[3,4-c]pyridine can be prepared in the following way:

15 mg of 3-(1H-benzimidazol-2-yl)-4,5,6,7-tetrahydro-2H-pyrazolo[3,4-c]-pyridine hydrochloride are suspended in 0.5 ml of methanol. 26.5 mg of 3-chlorobenzaldehyde are added, followed by 7.9 mg of NaBH$_3$CN. The reaction mixture is stirred at ambient temperature for 20 hours and is then concentrated under reduced pressure.

The evaporation residue is purified by LC/MS (method B). After purification by LC/MS, the fractions containing the 6-(3-chlorobenzyl)-3-(1H-benzoimidazol-2-yl)-4,5,6,7-tetrahydro-2H-pyrazolo[3,4-c]pyridine are combined and loaded onto SCX phase (500 mg of CUBCX1-HL phase). The SCX phase is subsequently washed with methanol and extracted with a solution of 2M ammonia in methanol. The extraction solution obtained is then concentrated under reduced pressure. 6.9 mg of 6-(3-chlorobenzyl)-3-(1H-benzoimidazol-2-yl)-4,5,6,7-tetrahydro-2H-pyrazolo[3,4-c]pyridine are thus obtained in the form of a white powder, the characteristics of which are as follows: LC/MS (method A): molecular ion detected: 364.22; retention time=2.19 minutes

EXAMPLE 7

Preparation of an Amide Library

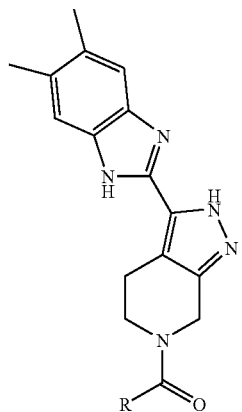

The amide library can be prepared in the following way;

The 19 acids (Table 4) are weighed and placed in 19 individual test tubes.

Table 4: Acids used

TABLE 4

Acids used

| Entry | Name | Amount |
|---|---|---|
| 1 | ISOBUTYRIC ACID | 3.3 mg |
| 2 | BENZOIC ACID | 4.6 mg |
| 3 | 2,3-DICHLOROBENZOIC ACID | 7.1 mg |
| 4 | PHENYLACETIC ACID | 5.1 mg |
| 5 | ACETIC ACID | 2.2 mg |
| 6 | CYCLOPROPANECARBOXYLIC ACID | 3.2 mg |
| 7 | 2-CHLOROBENZOIC ACID | 5.9 mg |
| 8 | 3-CHLOROBENZOIC ACID | 5.9 mg |
| 9 | 4-CHLOROBENZOIC ACID | 5.9 mg |
| 10 | ISOVALERIC ACID | 3.8 mg |
| 11 | HYDROCINNAMIC ACID | 5.6 mg |
| 12 | VINYLACETIC ACID | 3.2 mg |
| 13 | BUTYRIC ACID | 3.3 mg |
| 14 | 2-FUROIC ACID | 4.2 mg |
| 15 | PIVALIC ACID | 3.8 mg |
| 16 | N,N-DIMETHYLGLYCINE | 3.9 mg |
| 17 | VALERIC ACID | 3.8 mg |
| 18 | THIOPHENE-2-CARBOXYLIC ACID | 4.8 mg |
| 19 | 4-METHYLSULPHONYLBENZOIC ACID | 7.5 mg |

152 mg of HOBT and 142 mg of diisopropylcarbodiimide are solubilized in 12 ml of DMF and the solution obtained is distributed in each of the 19 test tubes, at a rate of 600 μl per tube.

200 mg of 3-(5,6-dimethyl-1H-benzimidazol-2-yl)-4,5,6,7-tetrahydro-2H-pyrazolo[3,4-c]pyridine hydrochloride are suspended in 4 ml of DMF in the presence of 290 mg of N,N-diisopropylethylamine, and the suspension obtained is distributed into each of the 19 test tubes, at a rate of 200 μl per tube.

The 19 reaction mixtures are shaken by means of orbital shaking at ambient temperature for 20 hours.

For each reaction mixture, a 10 μl sample is taken and diluted in 40 μl of DMSO (Gilson Liquid Handler Quad-Z 215). Each sample in solution in DMSO thus obtained is analysed by LC/MS (method A).

The 19 reaction mixtures are then evaporated to dryness and the evaporation residues are each solubilized in 500 µl of DMSO, and the solutions obtained are then purified by LC/MS (method B).

After purification by LC/MS, the fractions containing the desired compounds are (optionally combined) loaded onto SCX phase (500 mg of CUBCX1-HL phase). The SCX phases are subsequently washed with methanol and then extracted with a solution of 2M ammonia in methanol. The extraction solutions are collected in tared glass tubes, evaporated to dryness (Savant AES 2000 or Genevac HT8 centrifugal evaporator), weighed (Mettler Toledo Automated Workstation LA200) and diluted to 10 mM in DMSO (Gilson Liquid Handler Quad-Z 215). Each solution obtained is analysed by LC/MS (method A).

The following compounds (Table 5) were isolated and characterized by means of their retention time and molecular peak in mass spectrometry (method A).

TABLE 5

Amide library obtained

| Entry | Name | Amount of product obtained | Retention time (minutes) | Molecular ion detected |
|---|---|---|---|---|
| 1 | 1-[3-(5,6-Dimethyl-1H-benzoimidazol-2-yl)-2,4,5,7-tetrahydropyrazolo-[3,4-c]pyridin-6-yl]-2-methylpropan-1-one | 5.8 mg | 3.08 | 338.23 |
| 2 | [3-(5,6-Dimethyl-1H-benzoimidazol-2-yl)-2,4,5,7-tetrahydropyrazolo[3,4-c]-pyridin-6-yl]phenylmethanone | 6.8 mg | 2.68 | 372.21 |
| 3 | (2,3-Dichlorophenyl)-[3-(5,6-dimethyl-1H-benzoimidazol-2-yl)-2,4,5,7-tetrahydropyrazolo[3,4-c]pyridin-6-yl]-methanone | 12 mg | 3.05 | 440.13 |
| 4 | 1-[3-(5,6-Dimethyl-1H-benzoimidazol-2-yl)-2,4,5,7-tetrahydropyrazolo-[3,4-c]pyridin-6-yl]-2-phenylethanone | 7.9 mg | 2.99 | 386.23 |
| 5 | 1-[3-(5,6-Dimethyl-1H-benzoimidazol-2-yl)-2,4,5,7-tetrahydropyrazolo-[3,4-c]pyridin-6-yl]ethanone | 2.7 mg | 2.4 | 310.19 |
| 6 | Cyclopropyl-[3-(5,6-dimethyl-1H-benzoimidazol-2-yl)-2,4,5,7-tetrahydropyrazolo[3,4-c]pyridin-6-yl]-methanone | 3.4 mg | 2.57 | 336.21 |
| 7 | (2-Chlorophenyl)-[3-(5,6-dimethyl-1H-benzoimidazol-2-yl)-2,4,5,7-tetrahydropyrazolo[3,4-c]pyridin-6-yl]-methanone | 11.2 mg | 2.97 | 406.18 |
| 8 | (3-Chlorophenyl)-[3-(5,6-dimethyl-1H-benzoimidazol-2-yl)-2,4,5,7-tetrahydropyrazolo[3,4-c]pyridin-6-yl]-methanone | 12.1 mg | 3.31 | 406.16 |
| 9 | (4-Chlorophenyl)-[3-(5,6-dimethyl-1H-benzoimidazol-2-yl)-2,4,5,7-tetrahydropyrazolo[3,4-c]pyridin-6-yl]-methanone | 11.5 mg | 3.51 | 406.17 |
| 10 | 1-[3-(5,6-Dimethyl-1H-benzoimidazol-2-yl)-2,4,5,7-tetrahydropyrazolo[3,4-c]-pyridin-6-yl]-3-methylbutan-1-one | 4.8 mg | 2.72 | 352.24 |
| 11 | 1-[3-(5,6-Dimethyl-1H-benzoimidazol-2-yl)-2,4,5,7-tetrahydropyrazolo[3,4-c]-pyridin-6-yl]-3-phenylpropan-1-one | 11.9 mg | 2.95 | 400.24 |
| 12 | 1-[3-(5,6-Dimethyl-1H-benzoimidazol-2-yl)-2,4,5,7-tetrahydropyrazolo-[3,4-c]pyridin-6-yl]but-3-en-1-one | 10.1 mg | 2.72 | 336.22 |

TABLE 5-continued

Amide library obtained

| Entry | Name | Amount of product obtained | Retention time (minutes) | Molecular ion detected |
|---|---|---|---|---|
| 13 | 1-[3-(5,6-Dimethyl-1H-benzoimidazol-2-yl)-2,4,5,7-tetrahydropyrazolo-[3,4-c]pyridin-6-yl]butan-1-one | 7 mg | 2.66 | 338.23 |
| 14 | [3-(5,6-Dimethyl-1H-benzoimidazol-2-yl)-2,4,5,7-tetrahydropyrazolo[3,4-c]-pyridin-6-yl]furan-2-yl-methanone | 9.5 mg | 2.67 | 362.19 |
| 15 | 1-[3-(5,6-Dimethyl-1H-benzoimidazol-2-yl)-2,4,5,7-tetrahydropyrazolo[3,4-c]-pyridin-6-yl]-2,2-dimethylpropan-1-one | 9.3 mg | 2.8 | 352.24 |
| 16 | 2-Dimethylamino-1-[3-(5,6-dimethyl-1H-benzoimidazol-2-yl)-2,4,5,7-tetrahydro-pyrazolo[3,4-c]pyridin-6-yl]ethanone | 4.7 mg | 2.55 | 353.23 |
| 17 | 1-[3-(5,6-Dimethyl-1H-benzoimidazol-2-yl)-2,4,5,7-tetrahydropyrazolo[3,4-c]-pyridin-6-yl]pentan-1-one | 5.4 mg | 2.78 | 352.24 |
| 18 | [3-(5,6-Dimethyl-1H-benzoimidazol-2-yl)-2,4,5,7-tetrahydropyrazolo[3,4-c]-pyridin-6-yl]thiophen-2-yl-methanone | 7.2 mg | 2.75 | 378.17 |
| 19 | [3-(5,6-Dimethyl-1H-benzoimidazol-2-yl)-2,4,5,7-tetrahydropyrazolo[3,4-c]-pyridin-6-yl]-(4-methanesulphonyl-phenyl)methanone | 14.3 mg | 2.79 | 450.19 |

EXAMPLE 8

Preparation of a Sulphonamide Library

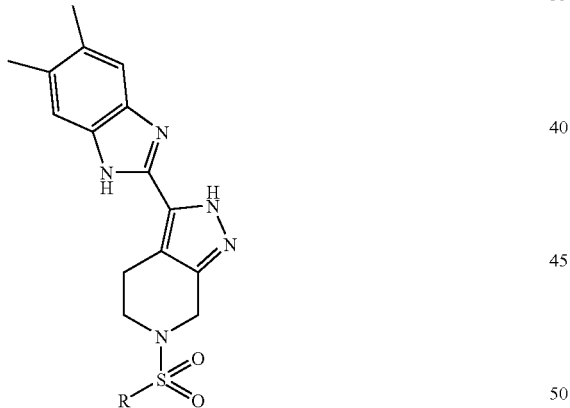

The sulphonamide library can be prepared in the following way:

190 mg of 3-(5,6-dimethyl-1H-benzimidazol-2-yl)-4,5,6,7-tetrahydro-2H-pyrazolo[3,4-c]pyridine hydrochloride are suspended in 2 ml of dichloromethane in the presence of 150 µl of triethylamine, and the suspension obtained is distributed into 17 test tubes, at a rate of 500 µl per tube. The 17 sulphonyl chlorides (Table 6) are weighed and added to each of the 17 test tubes.

TABLE 6

Sulphonyl chlorides used

| Entry | Name | Quantity |
|---|---|---|
| 1 | BENZENESULPHONYL CHLORIDE | 9.9 mg |
| 2 | ALPHA-TOLUENESULPHONYL CHLORIDE | 10.7 mg |
| 3 | 2,3-DICHLOROBENZENESULPHONYL CHLORIDE | 13.8 mg |
| 4 | 4-CHLOROBENZENESULPHONYL CHLORIDE | 11.9 mg |
| 5 | 2,2,2-TRIFLUOROETHANESULPHONYL CHLORIDE | 10.2 mg |
| 6 | ETHANESULPHONYL CHLORIDE | 7.2 mg |
| 7 | 1-PROPANESULPHONYL CHLORIDE | 8 mg |
| 8 | 1-BUTANESULPHONYL CHLORIDE | 8.8 mg |
| 9 | 2-CHLOROBENZENESULPHONYL CHLORIDE | 11.9 mg |
| 10 | 3-CHLOROBENZENESULPHONYL CHLORIDE | 11.9 mg |
| 11 | [(4-FLUOROPHENYL)METHYL]SULPHONYL CHLORIDE | 11.7 mg |
| 12 | 4-METHOXYBENZENESULPHONYL CHLORIDE | 11.6 mg |
| 13 | P-TOLUENESULPHONYL CHLORIDE | 10.7 mg |
| 14 | O-TOLUENESULPHONYL CHLORIDE | 10.7 mg |
| 15 | 3-METHYLBENZENESULPHONYL CHLORIDE | 10.7 mg |
| 16 | 3-METHOXYBENZENESULPHONYL CHLORIDE | 11.6 mg |
| 17 | 2-METHOXY-4-METHYLBENZENESULPHONYL CHLORIDE | 12.4 mg |

The 17 reaction mixtures are shaken by means of orbital shaking at ambient temperature for 20 h.

For each reaction mixture, a 10 µl sample is taken and diluted in 40 µl of DMSO (Gilson Liquid Handler Quad-Z 215). Each sample in solution in DMSO thus obtained is analysed by LC/MS (method A).

The 17 reaction mixtures are then evaporated to dryness and the evaporation residues are each solubilized in 1 ml of DMSO in the presence of a drop of an aqueous 5N hydrochloric acid solution, and the solutions obtained are purified by LC/MS (method B). After purification by LC/MS, the fractions containing the desired compounds are (optionally combined) loaded onto SCX phase (500 mg of CUBCX1-HL phase). The SCX phases are subsequently washed with methanol and then extracted with a solution of 2M ammonia in methanol. The extraction solutions are collected in tared glass tubes, evaporated to dryness (Savant AES 2000 or Genevac HT8 centrifugal evaporator), weighed (Mettler Toledo Automated Workstation LA200) and diluted to 10 mM in DMSO (Gilson Liquid Handler Quad-Z 215). Each solution obtained is analysed by LC/MS (method A).

The following compounds (Table 7) were isolated and characterized by means of their retention time and molecular peak in mass spectrometry (method A).

TABLE 7

Sulphonamide library obtained

| Entry | Name | Amount of product obtained | Retention time (minutes) | Molecular ion detected |
|---|---|---|---|---|
| 1 | 6-Benzenesulphonyl-3-(5,6-dimethyl-1H-benzoimidazol-2-yl)-4,5,6,7-tetrahydro-2H-pyrazolo[3,4-c]pyridine | 1.4 mg | 3.41 | 408.18 |
| 2 | 3-(5,6-Dimethyl-1H-benzoimidazol-2-yl)-6-phenylmethanesulphonyl-4,5,6,7-tetrahydro-2H-pyrazolo[3,4-c]pyridine | 0.7 mg | 3.51 | 422.2 |
| 3 | 6-(2,3-Dichlorobenzenesulphonyl)-3-(5,6-dimethyl-1H-benzoimidazol-2-yl)-4,5,6,7-tetrahydro-2H-pyrazolo-[3,4-c]pyridine | 6.4 mg | 3.25 | 476.1 |
| 4 | 6-(4-Chlorobenzenesulphonyl)-3-(5,6-dimethyl-1H-benzoimidazol-2-yl)-4,5,6,7-tetrahydro-2H-pyrazolo-[3,4-c]pyridine | 5.9 mg | 3.19 | 442.12 |
| 5 | 3-(5,6-Dimethyl-1H-benzoimidazol-2-yl)-6-(2,2,2-trifluoroethanesulphonyl)-4,5,6,7-tetrahydro-2H-pyrazolo-[3,4-c]pyridine | 1.7 mg | 3.06 | 414.14 |
| 6 | 3-(5,6-Dimethyl-1H-benzoimidazol-2-yl)-6-ethanesulphonyl-4,5,6,7-tetrahydro-2H-pyrazolo[3,4-c]pyridine | 5.2 mg | 2.63 | 360.17 |
| 7 | 3-(5,6-Dimethyl-1H-benzoimidazol-2-yl)-6-(propane-1-sulphonyl)-4,5,6,7-tetrahydro-2H-pyrazolo[3,4-c]pyridine | 4.3 mg | 2.8 | 374.19 |
| 8 | 6-(Butane-1-sulphonyl)-3-(5,6-dimethyl-1H-benzoimidazol-2-yl)-4,5,6,7-tetrahydro-2H-pyrazolo[3,4-c]pyridine | 5.6 mg | 2.94 | 388.2 |

TABLE 7-continued

Sulphonamide library obtained

| Entry | Name | Amount of product obtained | Retention time (minutes) | Molecular ion detected |
|---|---|---|---|---|
| 9 | 6-(2-Chlorobenzenesulphonyl)-3-(5,6-dimethyl-1H-benzoimidazol-2-yl)-4,5,6,7-tetrahydro-2H-pyrazolo[3,4-c]-pyridine | 5.6 mg | 3.38 | 442.13 |
| 10 | 6-(3-Chlorobenzenesulphonyl)-3-(5,6-dimethyl-1H-benzoimidazol-2-yl)-4,5,6,7-tetrahydro-2H-pyrazolo[3,4-c]-pyridine | 6.9 mg | 3.71 | 442.13 |
| 11 | 3-(5,6-Dimethyl-1H-benzoimidazol-2-yl)-6-(4-fluorophenylmethanesulphonyl)-4,5,6,7-tetrahydro-2H-pyrazolo[3,4-c]-pyridine | 0.7 mg | 3.05 | 440.18 |
| 12 | 3-(5,6-Dimethyl-1H-benzoimidazol-2-yl)-6-(4-methoxybenzenesulphonyl)-4,5,6,7-tetrahydro-2H-pyrazolo[3,4-c]-pyridine | 7.5 mg | 2.99 | 438.19 |
| 13 | 3-(5,6-Dimethyl-1H-benzoimidazol-2-yl)-6-(toluene-4-sulphonyl)-4,5,6,7-tetrahydro-2H-pyrazolo[3,4-c]pyridine | 7.3 mg | 3.22 | 422.2 |
| 14 | 3-(5,6-Dimethyl-1H-benzoimidazol-2-yl)-6-(toluene-2-sulphonyl)-4,5,6,7-tetrahydro-2H-pyrazolo[3,4-c]pyridine | 4.8 mg | 3.16 | 422.19 |
| 15 | 3-(5,6-Dimethyl-1H-benzoimidazol-2-yl)-6-(toluene-3-sulphonyl)-4,5,6,7-tetrahydro-2H-pyrazolo[3,4-c]pyridine | 5.1 mg | 3.13 | 422.19 |
| 16 | 3-(5,6-Dimethyl-1H-benzoimidazol-2-yl)-6-(3-methoxybenzenesulphonyl)-4,5,6,7-tetrahydro-2H-pyrazolo[3,4-c]-pyridine | 6.9 mg | 3.07 | 438.18 |
| 17 | 3-(5,6-Dimethyl-1H-benzoimidazol-2-yl)-6-(2-methoxy-4-methyl-benzene-sulphonyl)-4,5,6,7-tetrahydro-2H-pyrazolo[3,4-c]pyridine | 0.8 mg | 3.34 | 452.19 |

EXAMPLE 9

Preparation of an Amine Library

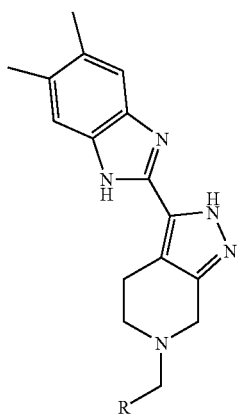

The amine library can be prepared in the following way:
180 mg of 3-(5,6-dimethyl-1H-benzimidazol-2-yl)-4,5,6,7-tetrahydro-2H-pyrazolo[3,4-c]pyridine hydrochloride are suspended in 2.7 ml of methanol and the suspension obtained is distributed into 16 test tubes, at a rate of 150 µl per tube.

The 16 aldehydes (Table 8) are weighed and added to each of the 16 test tubes.

TABLE 8

Aldehydes used

| Entry | Name | Quantity |
|---|---|---|
| 1 | ISOBUTYRALDEHYDE | 8.1 mg |
| 2 | FORMALDEHYDE | 3.4 mg |
| 3 | BENZALDEHYDE | 11.9 mg |
| 4 | PHENYLACETALDEHYDE | 13.5 mg |
| 5 | 2,3-DICHLOROBENZALDEHYDE | 19.6 mg |
| 6 | FURFURAL | 10.8 mg |
| 7 | 4-CHLOROBENZALDEHYDE | 15.8 mg |
| 8 | 2-THIOPHENECARBOXALDEHYDE | 12.6 mg |
| 9 | NICOTINALDEHYDE | 12 mg |
| 10 | TRIMETHYLACETALDEHYDE | 9.7 mg |
| 11 | ACETALDEHYDE | 4.9 mg |
| 12 | ISOVALERALDEHYDE | 9.7 mg |
| 13 | PROPIONALDEHYDE | 6.5 mg |
| 14 | 3-PHENYLPROPIONALDEHYDE | 15.1 mg |
| 15 | BUTYRALDEHYDE | 8.1 mg |
| 16 | CYCLOPROPANECARBOXALDEHYDE | 7.9 mg |

A solution of 85 mg of $NaBH_3CN$ in 2.7 ml of methanol is then also distributed into the 16 test tubes, at a rate of 150 µl per tube. The 16 reaction mixtures are shaken by means of orbital shaking at ambient temperature for 20 h. 100 µl of methanol are then added to each of the 16 tubes.

For each reaction mixture, a 10 µl sample is taken and diluted in 40 µl of DMSO (Gilson Liquid Handler Quad-Z 215). Each sample in solution in DMSO thus obtained is analysed by LC/MS (method A).

The 16 reaction mixtures are then evaporated to dryness and the evaporation residues are each solubilized in 500 µl of DMSO and filtered through sintered glass, and the residual solutions are then purified by LC/MS (method B). After purification by LC/MS, the fractions containing the desired compounds are (optionally combined) loaded onto SCX phase (500 mg of CUBCX1-HL phase). The SCX phases are subsequently washed with methanol and then extracted with a solution of 2M ammonia in methanol. The extraction solutions are collected in tared glass tubes, evaporated to dryness (Savant AES 2000 or Genevac HT8 centrifugal evaporator), weighed (Mettler Toledo Automated Workstation LA200) and diluted to 10 mM in DMSO (Gilson Liquid Handler Quad-Z 215). Each solution obtained is analysed by LC/MS (method A).

The following compounds (Table 9) were isolated and characterized by means of their retention time and molecular peak in mass spectrometry (method A).

TABLE 9

Amine library obtained

| Entry | Name | Amount of product obtained | Retention time (minutes) | Molecular ion detected |
| --- | --- | --- | --- | --- |
| 1 | 3-(5,6-Dimethyl-1H-benzoimidazol-2-yl)-6-isobutyl-4,5,6,7-tetrahydro-2H-pyrazolo[3,4-c]pyridine | 5.9 mg | 2.62 | 324.32 |
| 2 | 3-(5,6-Dimethyl-1H-benzoimidazol-2-yl)-6-methyl-4,5,6,7-tetrahydro-2H-pyrazolo[3,4-c]pyridine | 3.5 mg | 2.49 | 282.29 |
| 3 | 6-Benzyl-3-(5,6-dimethyl-1H-benzoimidazol-2-yl)-4,5,6,7-tetrahydro-2H-pyrazolo[3,4-c]pyridine | 8.2 mg | 2.74 | 358.3 |
| 4 | 3-(5,6-Dimethyl-1H-benzoimidazol-2-yl)-6-phenethyl-4,5,6,7-tetrahydro-2H-pyrazolo[3,4-c]pyridine | 6.4 mg | 2.84 | 372.32 |
| 5 | 6-(2,3-Dichlorobenzyl)-3-(5,6-dimethyl-1H-benzoimidazol-2-yl)-4,5,6,7-tetrahydro-2H-pyrazolo[3,4-c]pyridine | 8.6 mg | 2.95 | 426.23 |
| 6 | 3-(5,6-Dimethyl-1H-benzoimidazol-2-yl)-6-furan-2-ylmethyl-4,5,6,7-tetrahydro-2H-pyrazolo[3,4-c]pyridine | 5.9 mg | 2.64 | 348.27 |
| 7 | 6-(4-Chlorobenzyl)-3-(5,6-dimethyl-1H-benzoimidazol-2-yl)-4,5,6,7-tetrahydro-2H-pyrazolo[3,4-c]pyridine | 4.7 mg | 2.9 | 392.26 |
| 8 | 3-(5,6-Dimethyl-1H-benzoimidazol-2-yl)-6-thiophen-2-ylmethyl-4,5,6,7-tetrahydro-2H-pyrazolo[3,4-c]pyridine | 8.4 mg | 2.71 | 364.24 |
| 9 | 3-(5,6-Dimethyl-1H-benzoimidazol-2-yl)-6-pyridin-3-ylmethyl-4,5,6,7-tetrahydro-2H-pyrazolo[3,4-c]pyridine | 11.7 mg | 2.55 | 359.29 |
| 10 | 3-(5,6-Dimethyl-1H-benzoimidazol-2-yl)-6-(2,2-dimethylpropyl)-4,5,6,7-tetrahydro-2H-pyrazolo[3,4-c]pyridine | 3.7 mg | 2.72 | 338.32 |
| 11 | 3-(5,6-Dimethyl-1H-benzoimidazol-2-yl)-6-ethyl-4,5,6,7-tetrahydro-2H-pyrazolo[3,4-c]pyridine | 5 mg | 2.55 | 296.27 |
| 12 | 3-(5,6-Dimethyl-1H-benzoimidazol-2-yl)-6-(3-methylbutyl)-4,5,6,7-tetrahydro-2H-pyrazolo[3,4-c]pyridine | 5.9 mg | 2.76 | 338.3 |
| 13 | 3-(5,6-Dimethyl-1H-benzoimidazol-2-yl)-6-propyl-4,5,6,7-tetrahydro-2H-pyrazolo[3,4-c]pyridine | 6.4 mg | 2.62 | 310.29 |
| 14 | 3-(5,6-Dimethyl-1H-benzoimidazol-2-yl)-6-(3-phenylpropyl)-4,5,6,7-tetrahydro-2H-pyrazolo[3,4-c]pyridine | 4.2 mg | 2.97 | 386.31 |
| 15 | 6-Butyl-3-(5,6-dimethyl-1H-benzoimidazol-2-yl)-4,5,6,7-tetrahydro-2H-pyrazolo[3,4-c]pyridine | 4.5 mg | 2.68 | 324.28 |
| 16 | 6-Cyclopropylmethyl-3-(5,6-dimethyl-1H-benzoimidazol-2-yl)-4,5,6,7-tetrahydro-2H-pyrazolo[3,4-c]pyridine | 3.9 mg | 2.62 | 322.27 |

EXAMPLE 10

Preparation of a Urea Library

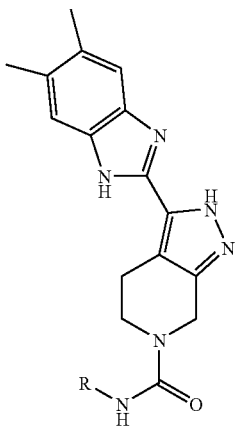

The urea library can be prepared in the following way:

120 mg of 3-(5,6-dimethyl-1H-benzimidazol-2-yl)-4,5,6,7-tetrahydro-2H-pyrazolo[3,4-c]pyridine hydrochloride are suspended in 3.6 ml of tetrahydrofuran in the presence of 190 µl of triethylamine, and the suspension obtained is distributed into each of the 9 test tubes, at a rate of 300 µl per tube.

The 9 isocyanates (Table 10) are weighed and added to each of the 9 test tubes.

TABLE 10

| | Isocyanates used | |
|---|---|---|
| Entry | Name | Amount |
| 1 | PHENYL ISOCYANATE | 6.7 mg |
| 2 | BENZYL ISOCYANATE | 7.5 mg |
| 3 | 2-CHLOROPHENYL ISOCYANATE | 8.6 mg |

TABLE 10-continued

| | Isocyanates used | |
|---|---|---|
| Entry | Name | Amount |
| 4 | 3-CHLOROPHENYL ISOCYANATE | 8.6 mg |
| 5 | 4-CHLOROPHENYL ISOCYANATE | 8.6 mg |
| 6 | N-BUTYL ISOCYANATE | 5.6 mg |
| 7 | 2-THIENYL ISOCYANATE | 7 mg |
| 8 | 2-METHOXYPHENYL ISOCYANATE | 8.4 mg |
| 9 | O-TOLYL ISOCYANATE | 7.5 mg |

The 9 reaction mixtures are shaken by means of orbital shaking at ambient temperature for 2 hours, and are then evaporated to dryness.

Evaporation residues are each solubilized in 1 ml of DMSO and, for each solution obtained, a 10 µl sample is taken and diluted in 40 µl of DMSO (Gilson Liquid Handler Quad-X 215). Each sample in solution in DMSO thus obtained is analysed by LC/MS (method A).

The residual solutions are purified by LC/MS (method B). After purification by LC/MS, the fractions containing the desired compounds are (optionally evaporated to dryness (entries 1, 3, 6, 8 and 9) or loaded onto SCX phase (500 mg of CUBCX1-HL phase; entries 2, 4, 5 and 7). The SCX phases are subsequently washed with methanol and then extracted with a solution of 2M ammonia in methanol. The extraction solutions are collected in tared glass, evaporated to dryness (Savant AES 2000 or Genevac HT8 centrifugal evaporator), weighed (Mettler Toledo Automated Workstation LA200) and diluted to 10 mM in DMSO (Gilson Liquid Handler Quad-Z 215). Each solution obtained is analysed by LC/MS (method A).

The following compounds (Table 11) were isolated and characterized by means of their retention time and molecular peak in mass spectrometry (method A).

TABLE 11

| | Urea library obtained | | | |
|---|---|---|---|---|
| Entry | Name | Amount of product obtained | Retention time (minutes) | Molecular ion detected |
| 1 | 3-(5,6-Dimethyl-1H-benzoimidazol-2-yl)-2,4,5,7-tetrahydropyrazolo[3,4-c]-pyridine-6-carboxylic acid phenylamide bistrifluoroacetate | 14.6 mg | 3.04 | 387.28 |
| 2 | 3-(5,6-Dimethyl-1H-benzoimidazol-2-yl)-2,4,5,7-tetrahydropyrazolo-[3,4-c]pyridine-6-carboxylic acid benzylamide | 1.8 mg | 2.78 | 401.29 |
| 3 | 3-(5,6-Dimethyl-1H-benzoimidazol-2-yl)-2,4,5,7-tetrahydropyrazolo-[3,4-c]pyridine-6-carboxylic acid (2-chlorophenyl)amide bistrifluoroacetate | 16 mg | 2.92 | 421.25 |
| 4 | 3-(5,6-Dimethyl-1H-benzoimidazol-2-yl)-2,4,5,7-tetrahydropyrazolo-[3,4-c]pyridine-6-carboxylic acid (3-chlorophenyl)amide | 7.9 mg | 3.89 | 421.24 |
| 5 | 3-(5,6-Dimethyl-1H-benzoimidazol-2-yl)-2,4,5,7-tetrahydropyrazolo- | 9.8 mg | 3.36 | 421.25 |

TABLE 11-continued

Urea library obtained

| Entry | Name | Amount of product obtained | Retention time (minutes) | Molecular ion detected |
|---|---|---|---|---|
| | [3,4-c]pyridine-6-carboxylic acid (4-chlorophenyl)amide | | | |
| 6 | 3-(5,6-Dimethyl-1H-benzoimidazol-2-yl)-2,4,5,7-tetrahydropyrazolo-[3,4-c]pyridine-6-carboxylic acid butylamide bistrifluoroacetate | 2.4 mg | 2.8 | 367.31 |
| 7 | 3-(5,6-Dimethyl-1H-benzoimidazol-2-yl)-2,4,5,7-tetrahydropyrazolo-[3,4-c]pyridine-6-carboxylic acid thiophen-2-ylamide | 3.8 mg | 2.77 | 393.24 |
| 8 | 3-(5,6-Dimethyl-1H-benzoimidazol-2-yl)-2,4,5,7-tetrahydropyrazolo-[3,4-c]pyridine-6-carboxylic acid (2-methoxyphenyl)amide bistrifluoroacetate | 14.4 mg | 3.14 | 417.28 |
| 9 | 3-(5,6-Dimethyl-1H-benzoimidazol-2-yl)-2,4,5,7-tetrahydropyrazolo-[3,4-c]pyridine-6-carboxylic acid o-tolylamide bistrifluoroacetate | 16.2 mg | 2.68 | 401.29 |

EXAMPLE 11

3-(5,6-Dimethyl-1H-benzimidazol-2-yl)-4,5,6,7-tetrahydro-2H-pyrazolo[3,4-c]pyridine

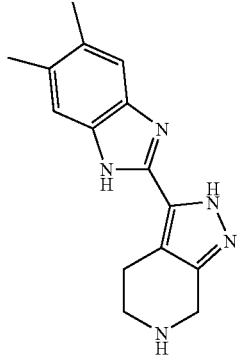

3-(5,6-Dimethyl-1H-benzimidazol-2-yl)-4,5,6,7-tetrahydro-2H-pyrazolo-[3,4-c]pyridine can be prepared in the following way:

9 ml of water and 2.8 ml of trifluoroacetic acid are added to a solution of 670 mg of tert-butyl 3-(2-amino-4,5-dimethylphenylcarbamoyl)-2,4,5,7-tetrahydropyrazolo[3,4-c]pyridine-6-carboxylate in 9 ml of THF. After stirring for 2 hours at 80° C., the reaction medium is concentrated under reduced pressure. It is then taken up in water and the precipitate formed is recovered by filtration through sintered glass, washed with an aqueous 1 N sodium hydroxide solution and dried. The aqueous phase obtained is subsequently extracted with dichloromethane and the organic phase is then dried over magnesium sulphate and concentrated under reduced pressure. The residue obtained and the precipitate are combined and then solubilized in methanol with a few drops of DMF. This solution is then loaded onto MEGA BE-SCX phase. The SCX phase is subsequently washed with methanol and extracted with a solution of 2M ammonia in methanol. The extraction solution obtained is then concentrated under reduced pressure.

46 mg of 3-(5,6-dimethyl-1H-benzimidazol-2-yl)-4,5,6,7-tetrahydro-2H-pyrazolo[3,4-c]pyridine are thus obtained in the form of a beige powder, the characteristics of which are as follows:

| EI: | m/z=267 | M$^{+\cdot}$ | base peak |
|---|---|---|---|
| | m/z=238 | [M —NHCH$_2$]$^+$ | |
| | m/z=209 | [M —C$_3$H$_8$N]$^{+\cdot}$ | |

$^1$H NMR (300 MHz, (CD$_3$)$_2$SO, δ in ppm): 2.31 and 2.32 (2 s: 6H in total); 2.81 (broad t, J=5 Hz: 2H); 2.92 (broad t, J=5 Hz: 2H); 3.83 (broad s: 2H); 7.22 (broad s; 1H); 7.40 (broad s: 1H); 12.28 (unresolved peak: 1H); 12.73 (unresolved peak: 1H).

EXAMPLE 12

3-(5,6-Dimethyl-1H-benzimidazol-2-yl)-4,5,6,7-tetrahydro-2H-pyrazolo[3,4-c]pyridine hydrochloride

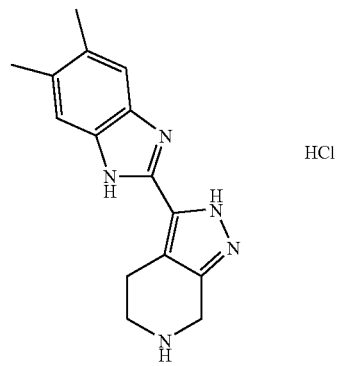

3-(5,6-Dimethyl-1H-benzimidazol-2-yl)-4,5,6,7-tetrahydro-2H-pyrazolo[3,4-c]pyridine can be prepared in the following way:

9 ml of an aqueous 5N hydrochloric acid solution are added to a solution of 1.7 g of tert-butyl 3-(2-amino-4,5-dimethylphenylcarbamoyl)-2,4,5,7-tetrahydropyrazolo[3,4-c]pyridine-6-carboxylate in 40 ml of ethanol. After stirring at 80° C. for 60 hours, the reaction medium is brought back to ambient temperature. The precipitate formed is recovered by filtration through sintered glass and dried. 1.04 g of 3-(5,6-dimethyl-1H-benzimidazol-2-yl)-4,5,6,7-tetrahydro-2H-pyrazolo[3,4-c]pyridine hydrochloride are thus obtained in the form of a beige powder, the characteristics of which are as follows:

| EI: | m/z = 267 | M+· | base peak |
|---|---|---|---|
| | m/z = 238 | [M – CH$_2$NH]+ | |
| | m/z = 209 | [M – C$_3$H$_8$N]+· | |
| | m/z = 36 | [HCl]+ | |

$^1$H NMR (300 MHz, (CD$_3$)$_2$SO with addition of a few drops of CD$_3$COOD, δ in ppm): 2.40 (s: 6H); 3.23 (broad t, J=5.5 Hz: 2H); 3.45 (t, J=5.5 Hz: 2H); 4.45 (s: 2H); 7.54 (s: 2H).

tert-Butyl 3-(2-amino-4,5-dimethylphenylcarbamoyl)-2,4,5,7-tetrahydro-pyrazolo[3,4-c]pyridine-6-carboxylate can be prepared in the following way:

8.5 g of HBTU and also 2.9 g of diisopropylethylamine are added, at ambient temperature, to a solution of 3 g of (tert-butyl 2,4,5,7-tetrahydropyrazolo-[3,4-c]pyridine-6-carboxylate)-3-carboxylic acid in 50 ml of anhydrous DMF. After twenty minutes' stirring at ambient temperature, 3.06 g of 4,5-diamino-o-xylene are added. After stirring at ambient temperature for 60 hours, the reaction medium is diluted in 3 l of an aqueous NaHCO$_3$ solution at pH greater than 7, containing 20 g of NaCl. The aqueous phase is extracted three times with 1 l of ethyl acetate, and the combined organic phases are then dried over magnesium sulphate and concentrated under reduced pressure. The crude residue obtained is taken up in 150 ml of dichloromethane and the insoluble material is removed by filtration through sintered glass. The filtrate is then concentrated under reduced pressure and purified by chromatography on silica (20-45 μm Amicon) with a gradient of from 50 to 100% of ethyl acetate in cyclohexane. The fractions containing the desired product are combined and concentrated under reduced pressure. 4.37 g of tert-butyl 3-(2-aminophenylcarbamoyl)-2,4,5,7-tetrahydro-pyrazolo [3,4-c]pyridine-6-carboxylate are thus obtained in the form of a beige powder, the characteristics of which are as follows:

| EI: | m/z = 385 | M+· | base peak |
|---|---|---|---|
| | m/z = 329 | [M – C$_4$H$_8$]+· | |
| | m/z = 312 | [M – C$_4$H$_9$O]+ | |
| | m/z = 57 | [C$_4$H$_9$]+ | |

$^1$H NMR (300 MHz, (CD$_3$)$_2$SO, δ in ppm): 1.46 (s: 9H); 2.10 and 2.12 (2 s: 3H each); 2.77 (mt: 2H); 3.58 (t, J=5.5 Hz: 2H); 4.53 (s: 2H); 4.57 (unresolved peak: 2H); 6.60 (s: 1H); 7.14 (broad s: 1H); 9.10 (unresolved peak: 1H); 13.08 (unresolved peak: 1H).

EXAMPLE 13

3-(1H-Benzimidazol-2-yl)-4,5,6,7-tetrahydro-2H-pyrazolo-[3,4-c]pyridine hydrochloride

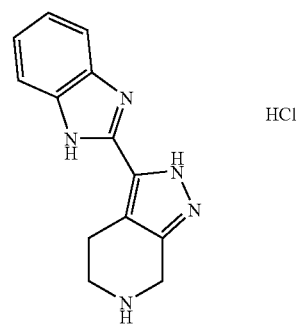

3-(1H-Benzimidazol-2-yl)-4,5,6,7-tetrahydro-2H-pyrazolo[3,4-c]pyridine hydrochloride can be prepared in the following way:

2.2 ml of an aqueous 5N hydrochloric acid solution are added to a solution of 200 mg of tert-butyl 3-(2-aminophenylcarbamoyl)-2,4,5,7-tetrahydro-pyrazolo[3,4-c]pyridine-6-carboxylate in 1 ml of ethanol. After stirring for 20 hours at 80° C., the reaction medium is brought back to ambient temperature. The insoluble material is removed by filtration through sintered glass and the filtrate is concentrated under reduced pressure. 84 mg of 3-(1H-benzimidazol-2-yl)-4,5,6,7-tetrahydro-2H-pyrazolo[3,4-c]pyridine hydrochloride are thus obtained in the form of an orange-coloured powder, the characteristics of which are as follows:

LC/MS (method A): molecular ion detected: 240.26; retention time=1.68 minutes tert-Butyl 3-(2-aminophenylcarbamoyl)-2,4,5,7-tetrahydro-pyrazolo[3,4-c]-pyridine-6-carboxylate can be prepared in the following way:

425 mg of HBTU and also 145 mg of diisopropylethylamine are added, at ambient temperature, to a solution of 150 mg of (tert-butyl 2,4,5,7-tetrahydro-pyrazolo[3,4-c]pyridine-6-carboxylate)-3-carboxylic acid in 1 ml of anhydrous DMF. After stirring for twenty minutes at ambient temperature, 121 mg of orthophenylenediamine are added.

After stirring at ambient temperature for 20 hours, the reaction medium is diluted in 100 ml of water and 50 ml of ethyl acetate. The aqueous phase is extracted three times with 50 ml of ethyl acetate and the combined organic phases are then dried over magnesium sulphate and concentrated under reduced pressure. The crude residue obtained is purified by HPLC (reverse phase C18 Lichroprep 12 μm) with a linear gradient of from 5 to 95% of acetonitrile comprising 0.07% (v/v) of trifluoroacetic acid in water comprising 0.07% (v/v) of trifluoroacetic acid, at a flow rate of 10 ml/min. The fractions containing the desired product are combined and loaded onto MEGA BE-SCX phase. The SCX phase is subsequently washed with methanol and extracted with a solution of 2M ammonia in methanol. The extraction solution obtained is then concentrated under reduced pressure. 200 mg of tert-butyl 3-(2-aminophenylcarbamoyl)-2,4,5,7-tetrahydropyrazolo[3,4-c]pyridine-6-carboxylate are thus obtained in the form of a beige powder, the characteristics of which are as follows:

LC/MS (method A): molecular ion detected: 358.34; retention time=3.19 minutes.

EXAMPLE 14

Preparation of a Sulphonamide Library

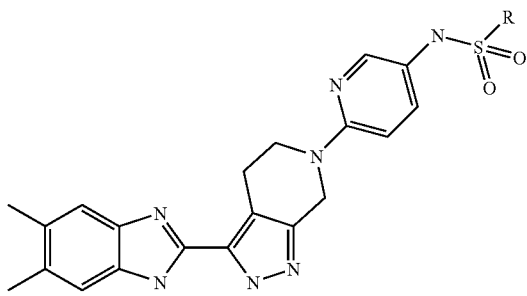

The sulphonamide library can be prepared in the following way:

40 mg of 6-[3-(5,6-dimethyl-1H-benzimidazol-2-yl)-2,4,5,7-tetrahydro-pyrazolo[3,4-c]pyridin-6-yl]pyridin-3-ylamine are suspended in 2 ml of dichloromethane and the solution obtained is distributed into 4 test tubes, at a rate of 500 µl per tube.

The 4 sulphonyl chlorides (Table 12) are weighed and added to each of the 4 test tubes, followed by 15.6 µl of triethylamine.

TABLE 12

Sulphonyl chlorides used

| Entry | Name | Amount |
|---|---|---|
| 1 | THIOPHENE-2-SULPHONYL CHLORIDE | 5.6 mg |
| 2 | 4-METHOXYBENZENESULPHONYL CHLORIDE | 6.3 mg |
| 3 | 2-CHLOROBENZENESULPHONYL CHLORIDE | 6.4 mg |
| 4 | 2-METHOXY-4-METHYLBENZENESULPHONYL CHLORIDE | 6.8 mg |

The 4 reaction mixtures are shaken by means of orbital shaking at 40° C. for 15 h.

For each reaction mixture, a 5 µl sample is taken and diluted in 100 µl of DMSO (Gilson Liquid Handler Quad-Z 215). Each sample in solution in DMSO thus obtained is analysed by LC/MS (method A).

The 4 reaction mixtures are then evaporated to dryness and the evaporation residues are each solubilized in 500 µl of DMSO and the solutions obtained are purified by LC/MS (method B). After purification by LC/MS, the fractions containing the desired compounds are (optionally combined) loaded onto SCX phase (500 mg of CUBCX1-HL phase). The SCX phases are subsequently washed with methanol and then extracted with a solution of 2M ammonia in methanol. The extraction solutions are collected in tared glass tubes, evaporated to dryness (Savant AES 2000 or Genevac HT8 centrifugal evaporator), weighed (Mettler Toledo Automated Workstation LA200) and diluted to 10 mM in DMSO (Gilson Liquid Handler Quad-Z 215). Each solution obtained is analysed by LC/MS (method A).

The following compounds (Table 13) were isolated and characterized by means of their retention time and molecular peak in mass spectrometry (method A)

TABLE 13

Sulphonamide library obtained

| Entry | Name | Amount of product obtained | Retention time (minutes) | Molecular ion detected |
|---|---|---|---|---|
| 1 | N-{6-[3-(5,6-Dimethyl-1H-benzimidazol-2-yl)-2,4,5,7-tetrahydropyrazolo[3,4-c]pyridin-6-yl]pyridin-3-yl}thiophene-2-sulphonamide | 2.9 mg | 3.07 | 506.21 |
| 2 | N-{6-[3-(5,6-Dimethyl-1H-benzimidazol-2-yl)-2,4,5,7-tetrahydropyrazolo[3,4-c]pyridin-6-yl]pyridin-3-yl}-4-methoxybenzenesulphonamide | 3.0 mg | 3.20 | 530.25 |
| 3 | 2-Chloro-N-{6-[3-(5,6-dimethyl-1H-benzimidazol-2-yl)-2,4,5,7-tetrahydropyrazolo[3,4-c]pyridin-6-yl]pyridin-3-yl}benzenesulphonamide | 3.0 mg | 3.38 | 534.21 |
| 4 | N-{6-[3-(5,6-Dimethyl-1H-benzimidazol-2-yl)-2,4,5,7-tetrahydropyrazolo[3,4-c]pyridin-6-yl]pyridin-3-yl}-2-methoxy-4-methylbenzenesulphonamide | 3.8 mg | 3.38 | 544.26 |

EXAMPLE 15

6-[3-(5,6-Dimethyl-1H-benzimidazol-2-yl)-2,4,5,7-tetrahydro-pyrazolo[3,4-c]pyridin-6-yl]pyridin-3-ylamine

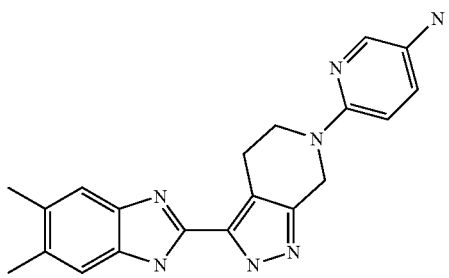

6-[3-(5,6-Dimethyl-1H-benzimidazol-2-yl)-2,4,5,7-tetrahydropyrazolo-[3,4-c]pyridin-6-yl]pyridin-3-ylamine can be prepared in the following way:

55 mg of Pd/CaCO$_3$ 10% are added to a solution of 545 mg of 3-(5,6-dimethyl-1H-benzimidazol-2-yl)-6-(5-nitropyridin-2-yl)-4,5,6,7-tetrahydro-2H-pyrazolo[3,4-c]pyridine in 60 ml of ethanol. After stirring for 15 hours at 35° C. under 3 bar of hydrogen, the reaction medium is brought back to ambient temperature, filtered through celite and then concentrated under reduced pressure. 300 mg of 6-[3-(5,6-dimethyl-1H-benzimidazol-2-yl)-2,4,5,7-tetrahydropyrazolo[3,4-c]pyridin-6-yl]-pyridin-3-ylamine are thus obtained in the form of a brown powder, the characteristics of which are as follows:

| EI | m/z = 359 | M$^{+.}$ | base peak |
|----|-----------|----------|-----------|
|    | m/z = 266 | (M – C$_5$H$_5$N$_2$)$^+$ | |

EXAMPLE 16

3-(5,6-Dimethyl-1H-benzimidazol-2-yl)-6-(5-nitro-pyridin-2-yl)-4,5,6,7-tetrahydro-2H-pyrazolo[3,4-c]pyridine

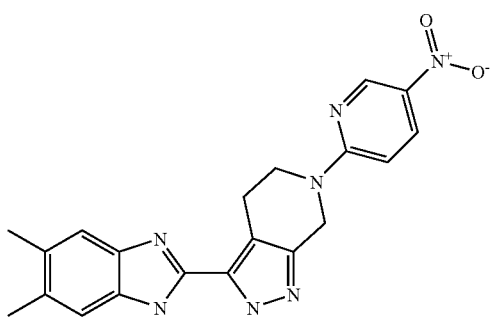

3-(5,6-Dimethyl-1H-benzimidazol-2-yl)-6-(5-nitropyridin-2-yl)-4,5,6,7-tetrahydro-2H-pyrazolo[3,4-c]pyridine can be prepared in the following way:

287 mg of 2-chloro-5-nitropyridine and 500 mg of potassium carbonate are added to a solution of 500 mg of 3-(5,6-dimethyl-1H-benzimidazol-2-yl)-4,5,6,7-tetrahydro-2H-pyrazolo[3,4-c]pyridine hydrochloride in 5 ml of dimethylformamide. After stirring for 20 hours at ambient temperature, the reaction medium is added to 50 ml of water. The precipitate formed is recovered by filtration through sintered glass, washed with 3 times 15 ml of water and then dried under reduced pressure. 548 mg of 3-(5,6-dimethyl-1H-benzimidazol-2-yl)-6-(5-nitropyridin-2-yl)-4,5,6,7-tetrahydro-2H-pyrazolo-[3,4-c]pyridine are thus obtained in the form of a yellow powder, the characteristics of which are as follows:

| EI: | m/z = 389 | M$^{+.}$ | base peak |
|-----|-----------|----------|-----------|
|     | m/z = 266 | (M – C$_5$H$_3$N$_2$O$_2$)$^+$ | |

EXAMPLE 17

6-{5-[3-(2-Fluoro-5-trifluoromethylphenyl)ureido]pyridin-2-yl}-4,5,6,7-tetrahydro-2H-pyrazolo[3,4-c]pyridine-3-carboxamide

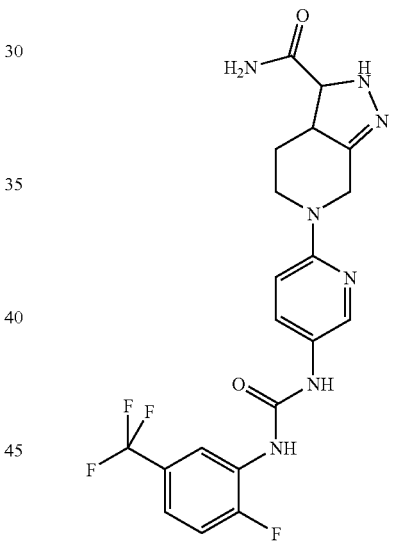

6-{5-[3-(2-Fluoro-5-trifluoromethylphenyl)ureido]pyridin-2-yl}-4,5,6,7-tetrahydro-2H-pyrazolo[3,4-c]pyridine-3-carboxamide can be prepared in the following way from ethyl 6-(5-tert-butoxycarbonylaminopyridin-2-yl)-4,5,6,7-tetrahydro-2H-pyrazolo[3,4-c]pyridine-3-carboxylate:

The ethyl ester of ethyl 6-(5-tert-butoxycarbonylaminopyridin-2-yl)-4,5,6,7-tetrahydro-2H-pyrazolo[3,4-c]pyridine-3-carboxylate is converted to carboxamide by amidation using a solution of aqueous ammonia, and results in the obtaining of 6-(5-tert-butoxycarbonylaminopyridin-2-yl)-4,5,6,7-tetrahydro-2H-pyrazolo[3,4-c]pyridine-3-carboxamide.

EI: m/z=358

The amine group of the 6-(5-tert-butoxycarbonylaminopyridin-2-yl)-4,5,6,7-tetrahydro-2H-pyrazolo[3,4-c]pyridine-3-carboxamide is deprotected in acid medium (trifluoroacetic acid in dichloromethane) and results in the obtaining of 6-(5-aminopyridin-2-yl)-4,5,6,7-tetrahydro-2H-pyrazolo[3,4-c]pyridine-3-carboxamide.

EI: m/z=358

The urea function is introduced onto the 6-(5-aminopyridin-2-yl)-4,5,6,7-tetrahydro-2H-pyrazolo[3,4-c]pyridine-3-carboxamide according to the method described in Example 1, using 2-fluoro-5-(trifluoromethyl)phenyl isocyanate, and results in the obtaining of 6-{5-[3-(2fluoro-5-trifluoromethylphenyl)-ureido]pyridin-2-yl}-4,5,6,7-tetrahydro-2H-pyrazolo[3,4-c]pyridine-3-carboxamide.

EI: m/z=463

EXAMPLE 18

Ethyl 6-(5-tert-butoxycarbonylaminopyridin-2-yl)-4,5,6,7-tetra-hydro-2H-pyrazolo[3,4-c]pyridine-3-carboxylate

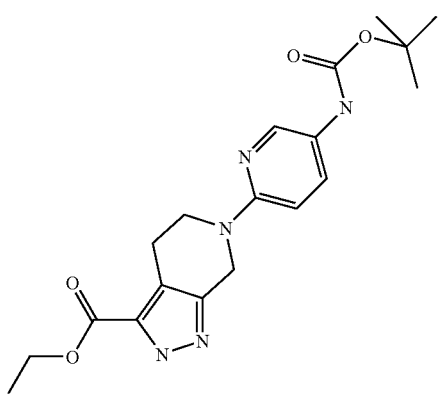

Ethyl 6-(5-tert-butoxycarbonylaminopyridin-2-yl)-4,5,6,7-tetrahydro-2H-pyrazolo[3,4-c]pyridine-3-carboxylate can be prepared in the following way:

5 mg of Pd/C 10% and 38 mg of di-tert-butyl dicarbonate are added to a solution of 50 mg of ethyl 6-(5-nitropyridin-2-yl)-4,5,6,7-tetrahydro-2H-pyrazolo[3,4-c]pyridine-3-carboxylate in 6 ml of methanol After stirring for 12 hours at ambient temperature under 3 bar of hydrogen, the reaction medium is filtered through celite and then concentrated under reduced pressure. The reaction crude obtained is purified by flash chromatography (SiO$_2$, CH$_2$Cl$_2$/MeOH gradient 75/25 to 25/75). 20 mg of ethyl 6-(5-tert-butoxycarbonylaminopyridin-2-yl)-4,5,6,7-tetrahydro-2H-pyrazolo[3,4-c]pyridine-3-carboxylate are thus obtained in the form of a white powder, the characteristics of which are as follows:

| EI: | m/z = 387 | M$^{+\cdot}$ | |
|---|---|---|---|
| | m/z = 331 | (M – C$_4$H$_8$)$^{+\cdot}$ | base peak |
| | m/z = 286 | (m/z = 331 – CO$_2$H)$^+$ | |
| | m/z = 194 | C$_9$H$_{12}$N$_3$O$_2{}^+$ | |
| | m/z = 57 | C$_4$H$_9{}^+$ | |

EXAMPLE 19

Ethyl 6-(5-nitropyridin-2-yl)-4,5,6,7-tetrahydro-2H-pyrazolo [3,4-c]pyridine-3-carboxylate

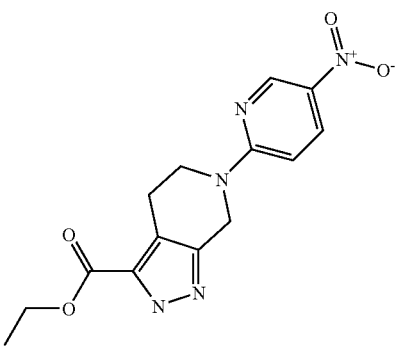

Ethyl 6-(5-nitropyridin-2-yl)-4,5,6,7-tetrahydro-2H-pyrazolo[3,4-c]pyridine-3-carboxylate can be prepared in the following way:

522 mg of 2-chloro-5-nitropyridine are added to a solution of 1 g of 3-(5,6-dimethyl-1H-benzimidazol-2-yl)-4,5,6,7-tetrahydro-2H-pyrazolo[3,4-c]pyridine trifluoroacetate in 10 ml of pyridine. After stirring for 20 hours at ambient temperature, the reaction medium is concentrated under reduced pressure. The precipitate formed is recovered by filtration through sintered glass, washed with 3 times 15 ml of water, and dried under reduced pressure. The reaction crude obtained is purified by flash chromatography (SiO$_2$, cyclohexane/EtOAc gradient 75/25 to 25/75). 450 mg of ethyl 6-(5-nitro-pyridin-2-yl)-4,5,6,7-tetrahydro-2H-pyrazolo[3,4-c]pyridine-3-carboxylate are thus obtained in the form of a yellow powder, the characteristics of which are as follows:

| EI: | m/z = 317 | M$^{+\cdot}$ | base peak |
|---|---|---|---|
| | m/z = 271 | (M – NO$_2$)$^{+\cdot}$ | |
| | m/z = 194 | (M – C$_5$H$_3$N$_2$O$_2$)$^+$ | |
| | m/z = 148 | (m/z = 194 – C$_2$H$_6$O)$^+$ | |

EXAMPLE 20

Ethyl 4,5,6,7-tetrahydro-2H-pyrazolo[3,4-c]pyridine-3-carboxylate trifluoroacetate

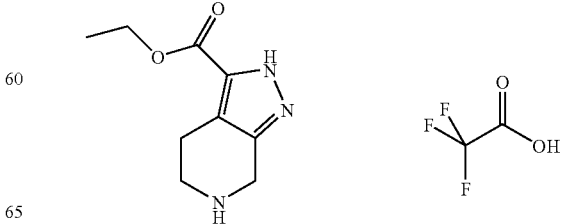

Ethyl 4,5,6,7-tetrahydro-2H-pyrazolo[3,4-c]pyridine-3-carboxylate trifluoro-acetate can be prepared in the following way:

50 ml of water followed by 12 ml of trifluoroacetic acid are added to a solution of 3 g of 6-tert-butyl-3-ethyl 2,4,5,7-tetrahydropyrazolo[3,4-c]pyridyl-3,6-dicarboxylate in 50 ml of tetrahydrofuran. After stirring for 2 hours at reflux, the reaction medium is brought back to ambient temperature and a saturated aqueous $Na_2CO_3$ solution is added until a basic pH is obtained. The aqueous phase obtained is extracted 3 times with ethyl acetate. The combined organic phases are dried over magnesium sulphate and concentrated under reduced pressure. 1.49 g of ethyl 4,5,6,7-tetrahydro-2H-pyrazolo[3,4-c]pyridine-3-carboxylate trifluoroacetate are thus obtained, the characteristics of which are as follows:

| EI: | m/z = 195 | $M^{+\cdot}$ | |
|---|---|---|---|
| | m/z = 166 | $(M - CH_3N)^{+\cdot}$ | base peak |
| | m/z = 138 | $(M - C_3H_7N)^{+\cdot}$ | |
| | m/z = 120 | $(m/z = 166 - C_2H_6O)^{+\cdot}$ | |
| | m/z = 92 | $(m/z = 120 - CO)^{+\cdot}$ | |

Measurements of the Inhibitory Potential of the Products with Respect to the Activity of the Tie2 and KDR Kinases:

The inhibitory activity of the products with respect to the Tie2 and KDR kinases is tested according to the experimental protocols described below.

1. Tie2

The coding sequence of human Tie2 corresponding to amino acids 776-1124 of the intracellular domain was generated by PCR using the cDNA isolated from human placenta as model. This sequence was introduced into a baculovirus expression vector pFastBacGT in the form of a GST fusion protein.

The inhibitory effect of the molecules is determined in an assay for phosphorylation of PLC by Tie2 in the presence of GST-Tie2 purified to approximately 80% homogeneity. The substrate is made up of the SH2-SH3 fragments of PLC, the latter being expressed in the form of a GST fusion protein.

The kinase activity of Tie2 is measured in a 20 mM MOPS buffer, pH 7.2, containing 10 mM $MgCl_2$, 10 mM $MnCl_2$, 1 mM DTT and 10 mM of glycerophosphate. A reaction mixture made up of 70 µl of kinase buffer containing 100 ng of GST-Tie2 enzyme per well is placed in a flashplate 96-well plate kept on ice. 10 µl of the molecule to be tested, diluted in DMSO, at a concentration of at most 10% are then added. For a given concentration, each measurement is carried out in quadruplicate. The reaction is initiated by adding 20 µl of solution containing 2 µg of GST-PLC, 2 µM of cold ATP and 1 µCi of $^{33}P[ATP]$. After incubation for 1 hour at 37° C., the reaction is stopped by adding 1 volume (100 µl) of 200 mM EDTA. After removal of the incubation buffer, the wells are washed three times with 300 µl of PBS. The radioactivity is measured on a Wallac MicroBeta 1450.

The inhibition of the Tie2 activity is calculated and expressed as percentage inhibition with respect to the control activity determined in the absence of compound.

2. KDR

The inhibitory effect of the compounds is determined in an assay for phosphorylation of substrate by the KDR enzyme in vitro using a scintillation technique (96-well plate, NEN).

The cytoplasmic domain of the human KDR enzyme was cloned in GST fusion form into the baculovirus expression vector pFastBac. The protein was expressed in SF21 cells and purified to approximately 60% homogeneity. The KDR kinase activity is measured in 20 mM MOPS, 10 mM $MgCl_2$, 10 mM $MnCl_2$, 1 mM DTT, 2.5 mM EGTA, 10 mM b-glycerophosphate, pH=7.2, in the presence of 10 mM $MgCl_2$, 100 µM $Na_3VO_4$ and 1 mM NaF. 10 µl of the compound are added to 70 µl of kinase buffer containing 100 ng of KDR enzyme at 4° C. The reaction is initiated by adding 20 µl of solution containing 2 µg of substrate (SH2-SH3 fragment of PLCγ expressed in the form of an GST fusion protein), 2 µCi γ $^{33}P[ATP]$ and 2 µM cold ATP. After incubation for 1 hour at 37° C., the reaction is stopped by adding 1 volume (100 µl) of 200 mM EDTA. The incubation buffer is removed and the wells are washed three times with 300 µl of PBS. The radioactivity is measured in each well using a Top Count NXT (Packard) radioactivity counter.

The background noise is determined by measuring the radioactivity in four different wells containing the radioactive ATP and the substrate alone.

A total activity control is measured in four different wells containing all the reagents (γ$^{33}$P-[ATP], KDR and PLC-γ substrate) but in the absence of compound.

The inhibition of the KDR activity with the compound of the invention is expressed as percentage inhibition of the control activity determined in the absence of compound.

The compound SU5614 (Calbiochem) (1 µM) is included in each plate as inhibition control.

Results:
| Chemistry | Tie2 % Inhib at 10 μM (FRX) | | KDR % Inhib at 10 μM | |
|---|---|---|---|---|
| | Assay 1 | Assay 2 | Assay 1 | Assay 2 |
| P-31378-112-3  | 78.7 | 79.1 | 59.0 | 56.5 |
| P-31378-112-6 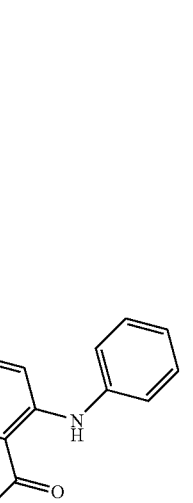 | 92.7 | 93.8 | 71.4 | 68.0 |
| P-31378-112-2  | 92.6 | 92.6 | 98.1 | 97.4 |

| Chemistry | Tie2 % Inhib at 10 μM (FRX) | | KDR % Inhib at 10 μM | |
|---|---|---|---|---|
| | Assay 1 | Assay 2 | Assay 1 | Assay 2 |
| P-31378-112-8 | 87.8 | 93.3 | 86.8 | 89.0 |
| P-31378-112-4 | 83.1 | 87.2 | 56.2 | 50.1 |
| P-31378-112-9 | 82.6 | 85.9 | 53.2 | 45.1 |
| P-31378-112-14 | 69.7 | 73.8 | 19.5 | 13.0 |

-continued

| Chemistry | Tie2 % Inhib at 10 μM (FRX) | | KDR % Inhib at 10 μM | |
|---|---|---|---|---|
| | Assay 1 | Assay 2 | Assay 1 | Assay 2 |
| P-31378-112-1 | 83.1 | 88.1 | 96.5 | 96.7 |
| P-31378-112-16 | 88.7 | 88.3 | 90.2 | 89.1 |
| P-31378-112-5 | 87.1 | 86.4 | 94.7 | 95.4 |
| P-31375-112-10 | 90.6 | 87.9 | 42.3 | 28.7 |

| Chemistry | Tie2 % Inhib at 10 µM (FRX) | | KDR % Inhib at 10 µM | |
|---|---|---|---|---|
| | Assay 1 | Assay 2 | Assay 1 | Assay 2 |
| P-31378-112-7 | 92.7 | 92.0 | 68.6 | 64.3 |
| P-31378-112-15 | 80.1 | 83.8 | 75.5 | 77.4 |
| Chemistry | KDR % Inhib. 10 µM | Tie2 % Inhib. 10 µM |
|---|---|---|
| Chemistry 2 | 77.20 | |
| Chemistry 3 | 78.10 | |
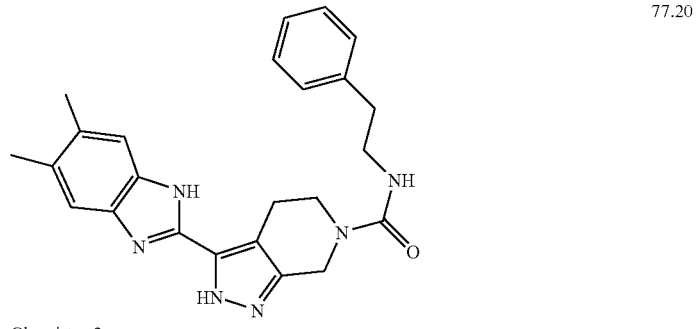
Chemistry 2
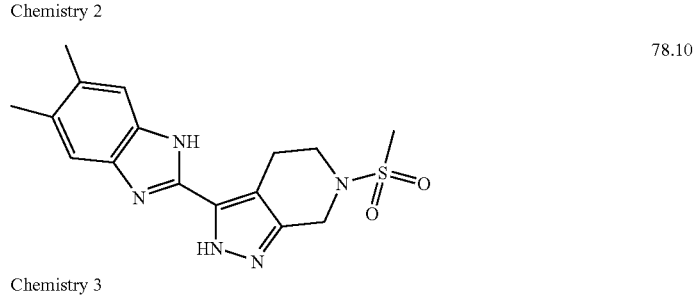
Chemistry 3

| Chemistry | KDR % Inhib. 10 μM | Tie2 % Inhib. 10 μM |
|---|---|---|
| 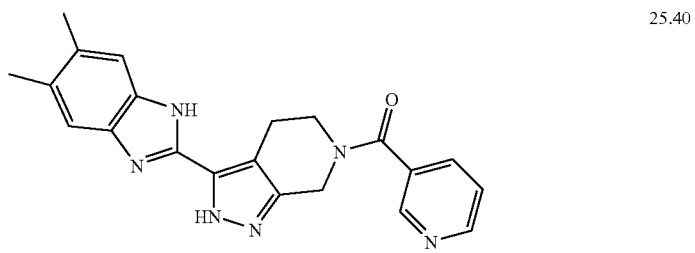<br>Chemistry 4 | 25.40 | |
| 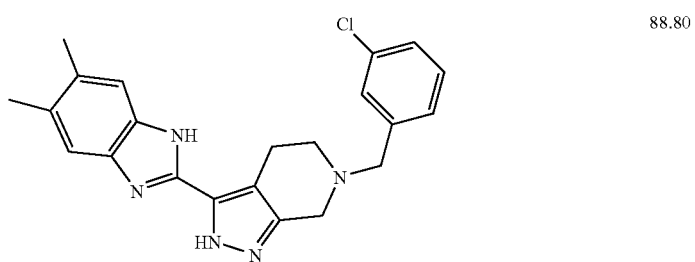<br>Chemistry 5 | 88.80 | |
| 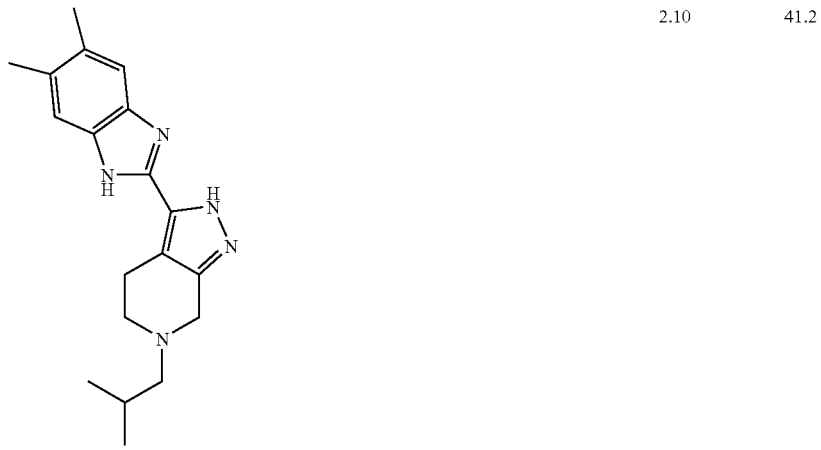<br>Chemistry 6 | 2.10 | 41.2 |
| 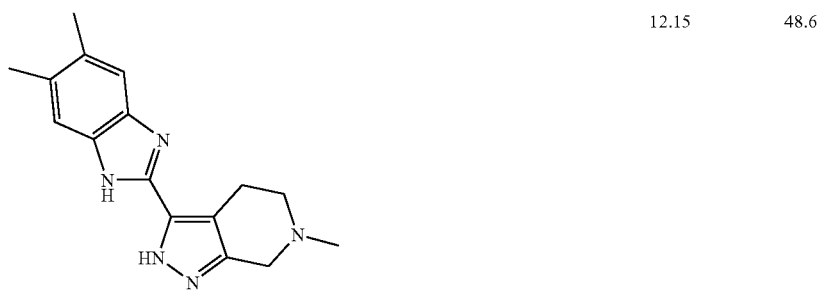<br>Chemistry 7 | 12.15 | 48.6 |

-continued
| Chemistry | KDR % Inhib. 10 μM | Tie2 % Inhib. 10 μM |
|---|---|---|
| 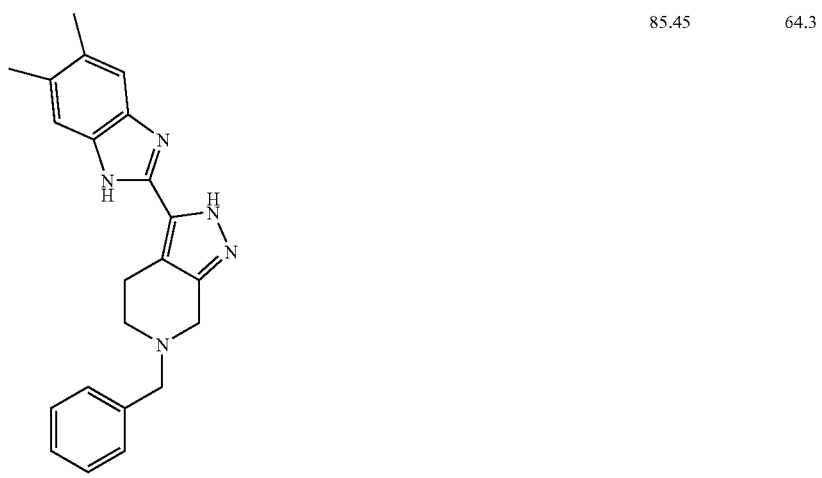
Chemistry 8 | 85.45 | 64.3 |
| 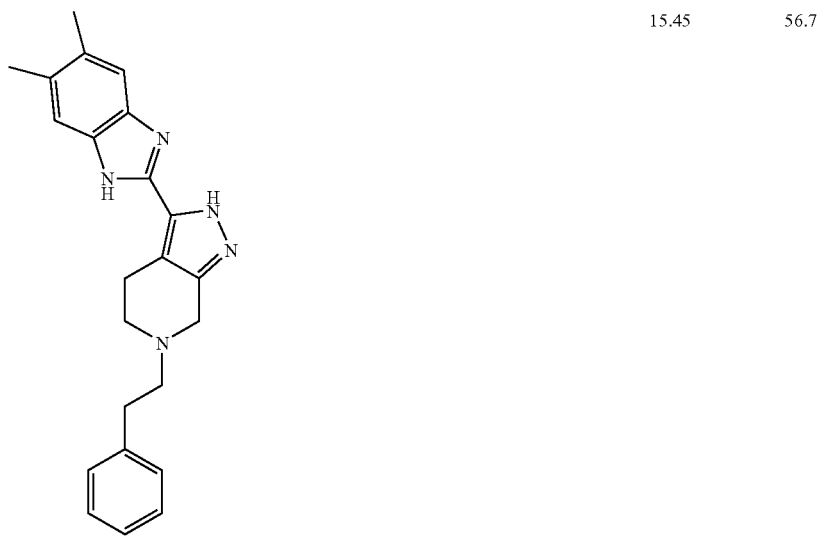
Chemistry 9 | 15.45 | 56.7 |
| 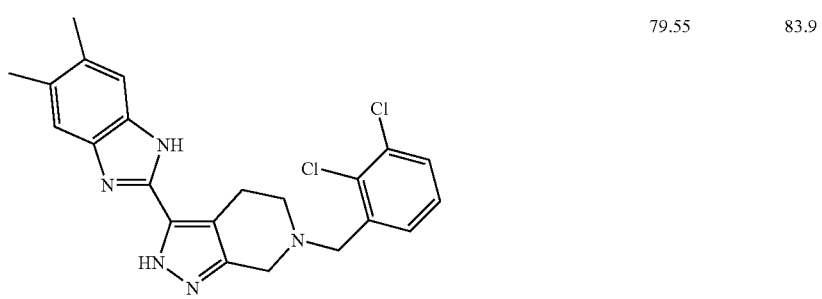
Chemistry 10 | 79.55 | 83.9 |

-continued
| Chemistry | KDR % Inhib. 10 μM | Tie2 % Inhib. 10 μM |
|---|---|---|
| 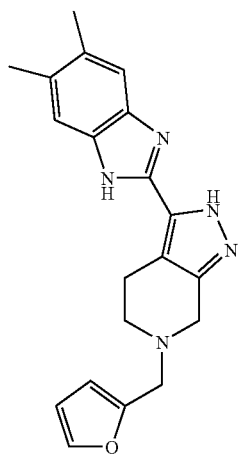<br>Chemistry 11 | 70.35 | 66.1 |
| 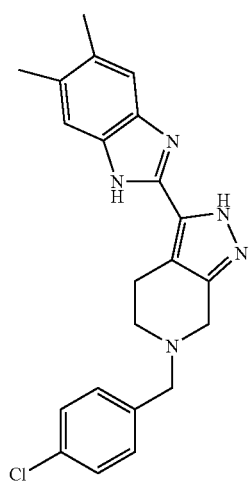<br>Chemistry 12 | 69.05 | 60.3 |
| 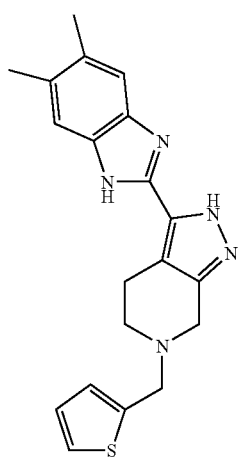<br>Chemistry 13 | 84.50 | 41.5 |

-continued
| Chemistry | KDR % Inhib. 10 μM | Tie2 % Inhib. 10 μM |
|---|---|---|
| 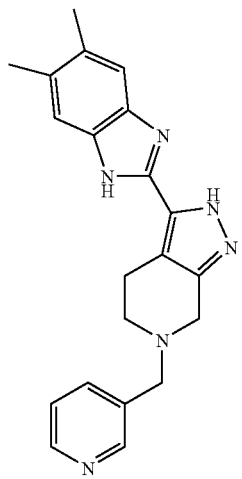<br>Chemistry 14 | 14.85 | 50.5 |
| 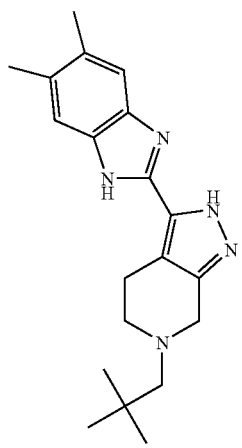<br>Chemistry 15 | 39.30 | 69.4 |
| 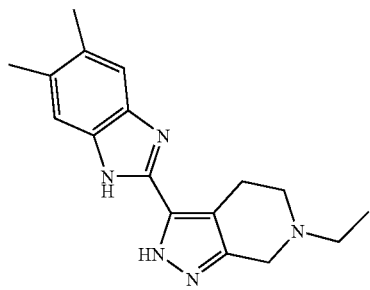<br>Chemistry 16 | −5.75 | 36.4 |

-continued

| Chemistry | KDR % Inhib. 10 μM | Tie2 % Inhib. 10 μM |
|---|---|---|
| Chemistry 17 | −2.90 | 50.7 |
| Chemistry 18 | −3.70 | 55.0 |
| Chemistry 19 | 17.90 | 68.1 |

| Chemistry | KDR % Inhib. 10 μM | Tie2 % Inhib. 10 μM |
|---|---|---|
| Chemistry 20 | 1.65 | 47.6 |
| Chemistry 21 | 1.85 | 33.0 |
| Chemistry 22 | 3.65 | 24.9 |
| Chemistry 23 | 48 | 92.5 |

-continued
| Chemistry | KDR % Inhib. 10 μM | Tie2 % Inhib. 10 μM |
|---|---|---|
| 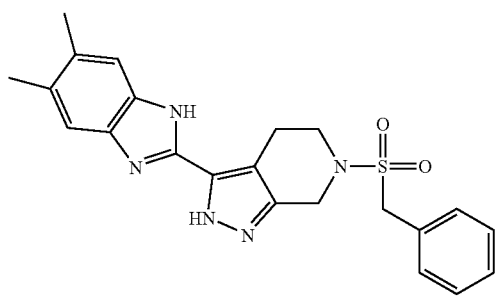  Chemistry 24 | 70.75 | 91.5 |
| 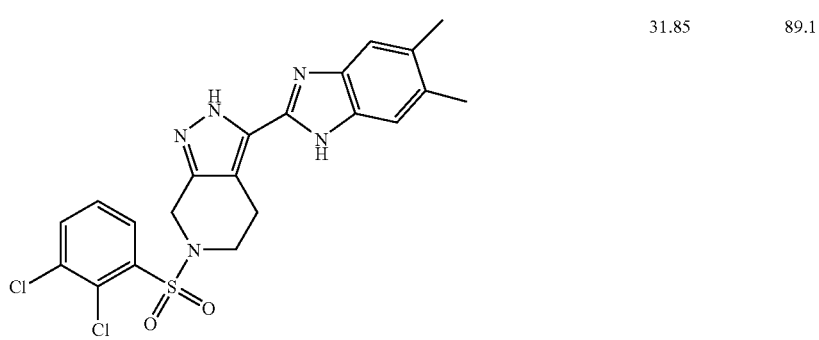  Chemistry 25 | 31.85 | 89.1 |
| 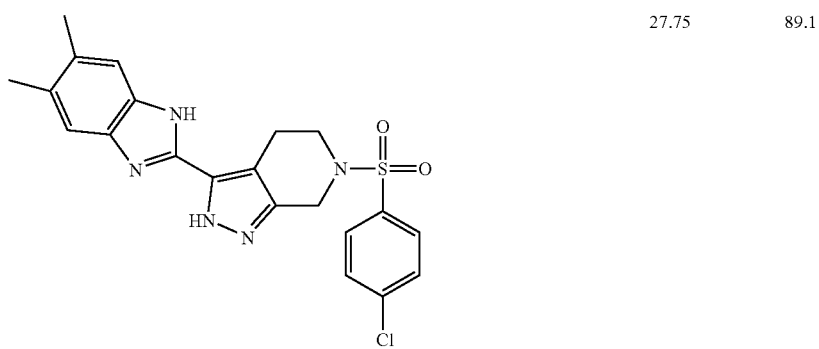  Chemistry 26 | 27.75 | 89.1 |
| 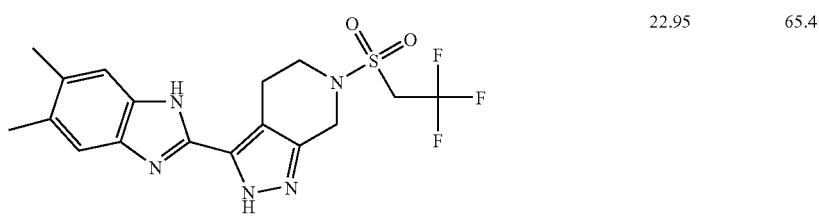  Chemistry 27 | 22.95 | 65.4 |

| Chemistry | KDR % Inhib. 10 μM | Tie2 % Inhib. 10 μM |
|---|---|---|
| Chemistry 28 | 16.50 | 78.5 |
| Chemistry 29 | 13.35 | 47.5 |
| Chemistry 30 | 15.30 | 44.2 |

-continued
| Chemistry | KDR % Inhib. 10 μM | Tie2 % Inhib. 10 μM |
|---|---|---|
| 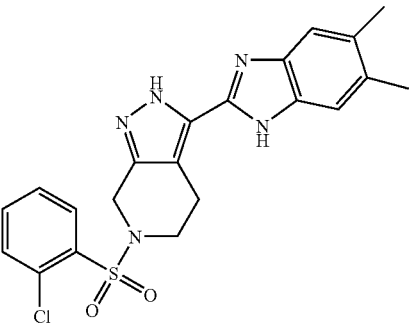 Chemistry 31 | 45.70 | 93.2 |
| 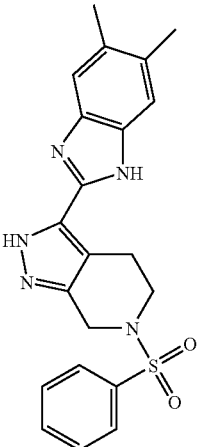 Chemistry 32 | 46.45 | 91.5 |
| 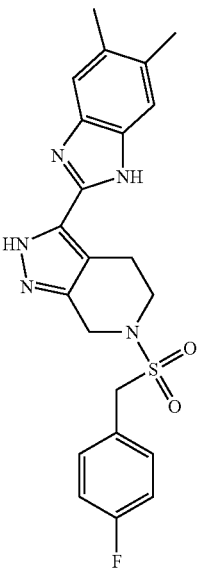 Chemistry 33 | 57.70 | 95.9 |

| Chemistry | KDR % Inhib. 10 μM | Tie2 % Inhib. 10 μM |
|---|---|---|
| 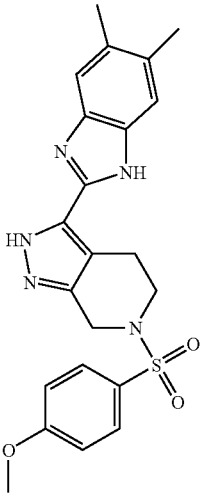
Chemistry 34 | 18.15 | 84.7 |
| 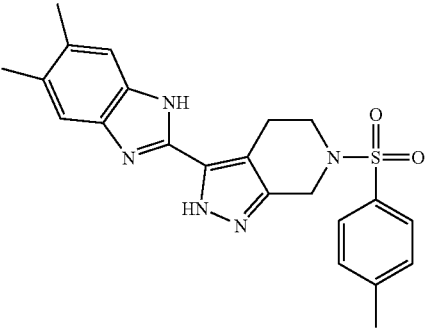
Chemistry 35 | 27.40 | 88.8 |
| 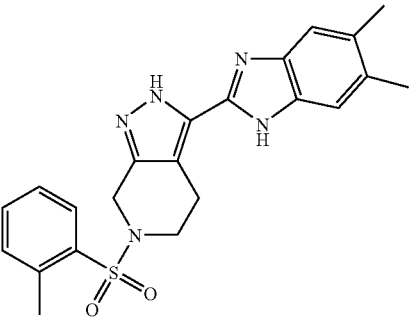
Chemistry 36 | 49.40 | 90.8 |

-continued
| Chemistry | KDR % Inhib. 10 μM | Tie2 % Inhib. 10 μM |
|---|---|---|
| 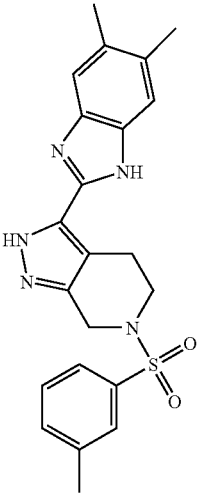<br>Chemistry 37 | 41.20 | 88.3 |
| 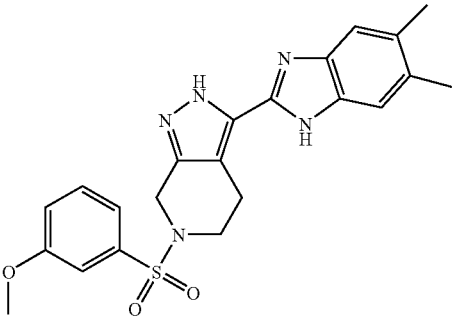<br>Chemistry 38 | 20.85 | 84.6 |
| 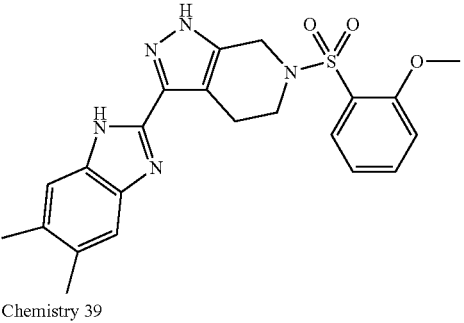<br>Chemistry 39 | 30.90 | 97.9 |

-continued
| Chemistry | KDR % Inhib. 10 μM | Tie2 % Inhib. 10 μM |
|---|---|---|
| 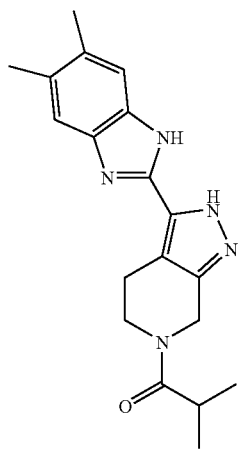<br>Chemistry 40 | 14.40 | 83.4 |
| 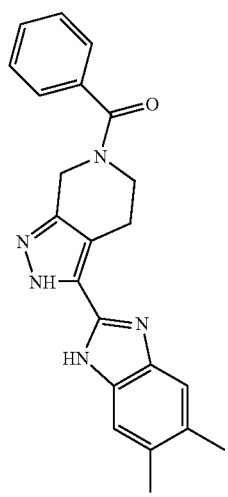<br>Chemistry 41 | 72.50 | 86.3 |
| 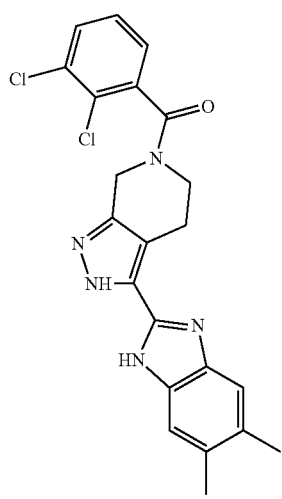<br>Chemistry 42 | 52.65 | 97.4 |

-continued
| Chemistry | KDR % Inhib. 10 μM | Tie2 % Inhib. 10 μM |
|---|---|---|
| 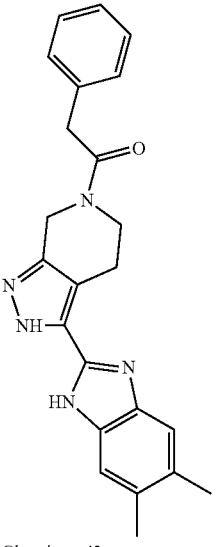  Chemistry 43 | 10.90 | 84.4 |
| 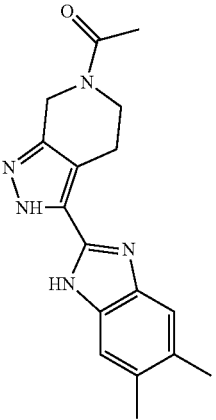  Chemistry 44 | 41.10 | 90.8 |
| 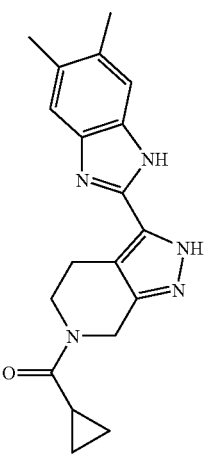  Chemistry 45 | 33.40 | 94.1 |

-continued
| Chemistry | KDR % Inhib. 10 μM | Tie2 % Inhib. 10 μM |
|---|---|---|
| 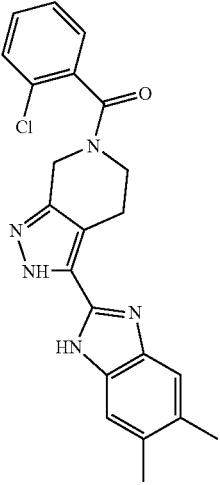<br>Chemistry 46 | 73.05 | 96.7 |
| 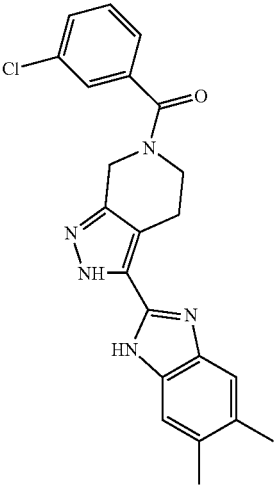<br>Chemistry 47 | 78.55 | 87.7 |
| 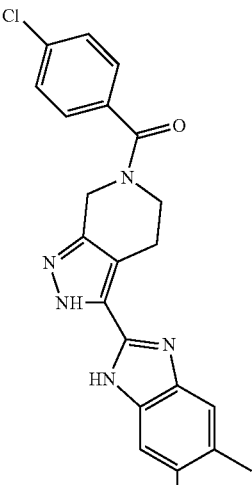<br>Chemistry 48 | 41.95 | 83.8 |

-continued
| Chemistry | KDR % Inhib. 10 μM | Tie2 % Inhib. 10 μM |
|---|---|---|
| 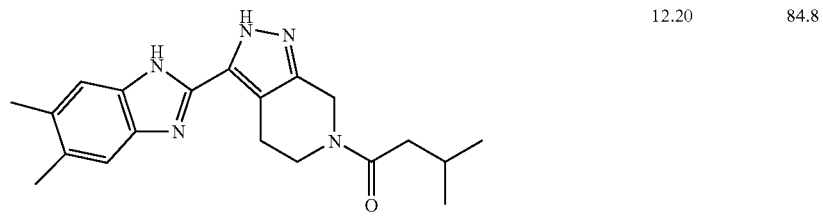
Chemistry 49 | 12.20 | 84.8 |
| 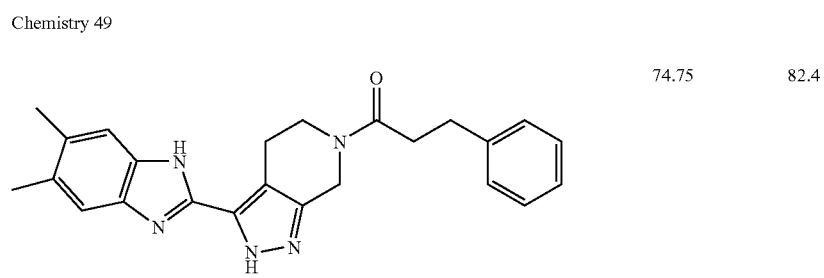
Chemistry 50 | 74.75 | 82.4 |
| 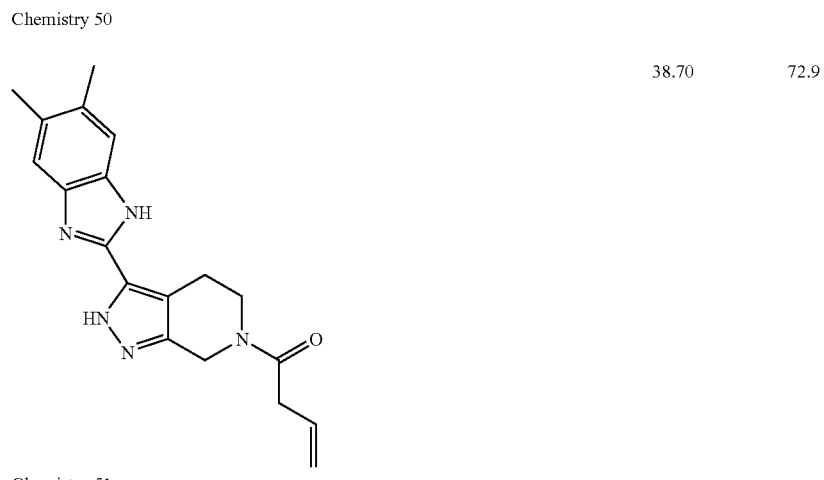
Chemistry 51 | 38.70 | 72.9 |
| 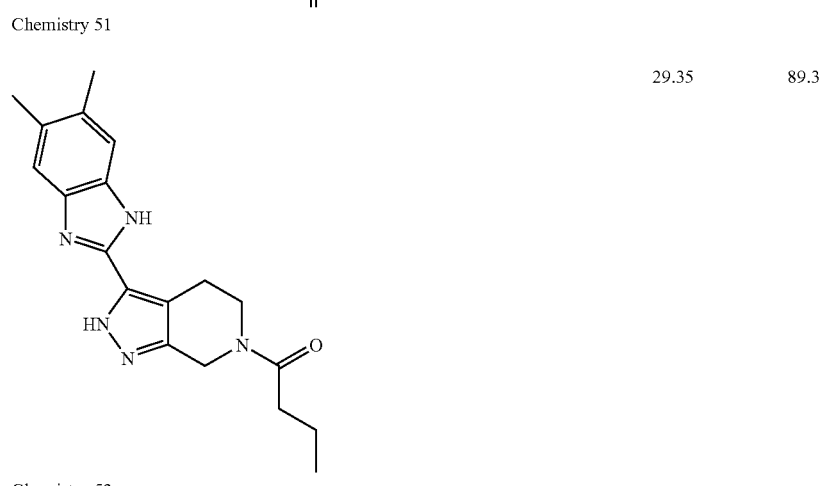
Chemistry 52 | 29.35 | 89.3 |

-continued
| Chemistry | KDR % Inhib. 10 µM | Tie2 % Inhib. 10 µM |
|---|---|---|
| 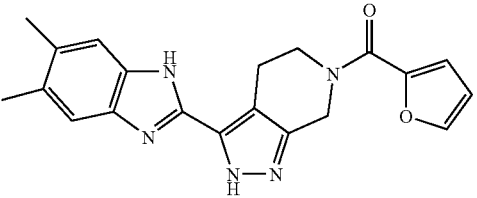<br>Chemistry 53 | 74.55 | 92.7 |
| 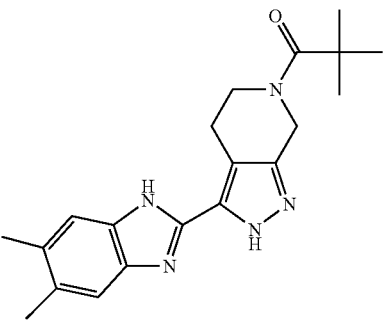<br>Chemistry 54 | 11.25 | 81.3 |
| 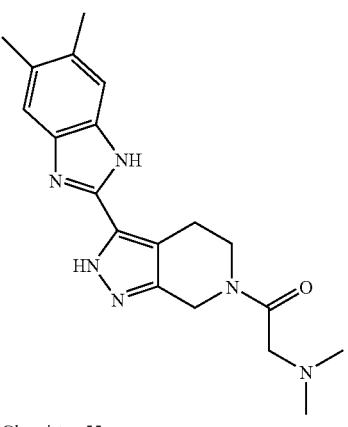<br>Chemistry 55 | 15.95 | 65.4 |
| 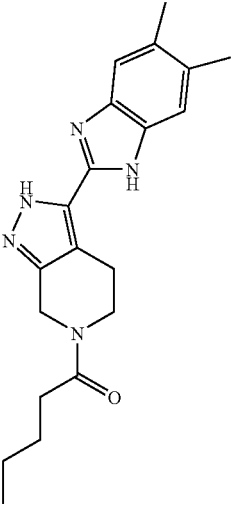<br>Chemistry 56 | 46.65 | 92.5 |

-continued

| Chemistry | KDR % Inhib. 10 μM | Tie2 % Inhib. 10 μM |
|---|---|---|
| Chemistry 57 | 75.15 | 94.6 |
| Chemistry 58 | 27.90 | 82.3 |
| Chemistry 59 | 17.6 | 33.2 |
| Chemistry 60 | 33.55 | 64.85 |

-continued
| Chemistry | KDR % Inhib. 10 μM | Tie2 % Inhib. 10 μM |
|---|---|---|
| 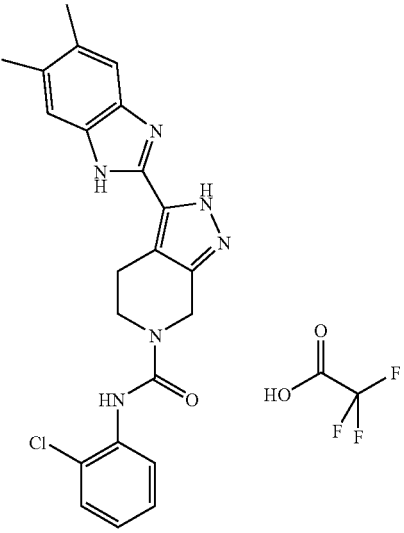<br>Chemistry 61 | 12.7 | 3.75 |
| 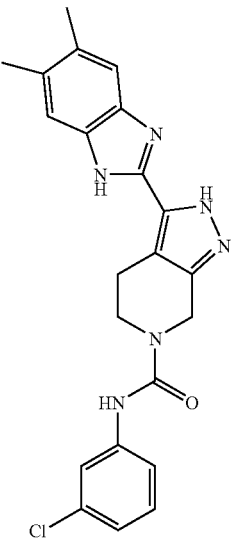<br>Chemistry 62 | 12.85 | 21 |

-continued
| Chemistry | KDR % Inhib. 10 μM | Tie2 % Inhib. 10 μM |
|---|---|---|
| 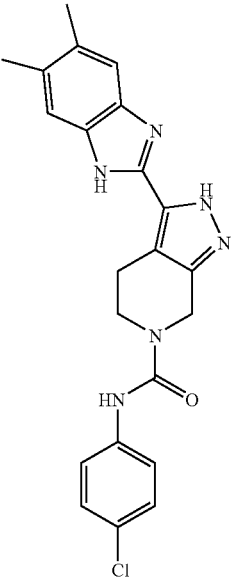 Chemistry 63 | −0.3 | 23.75 |
| 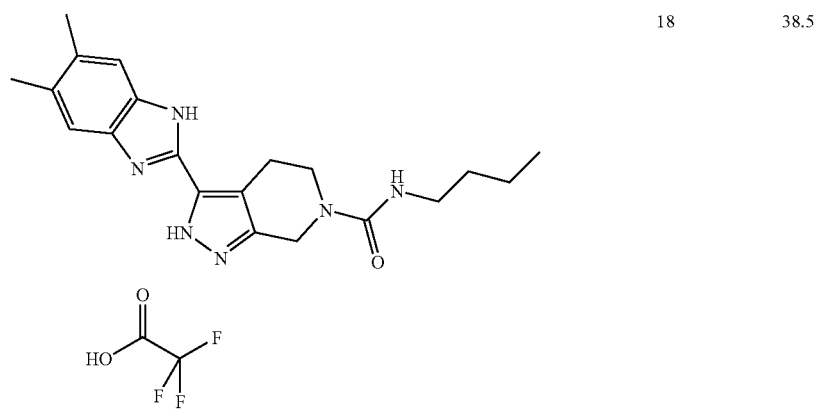 Chemistry 64 | 18 | 38.5 |
| 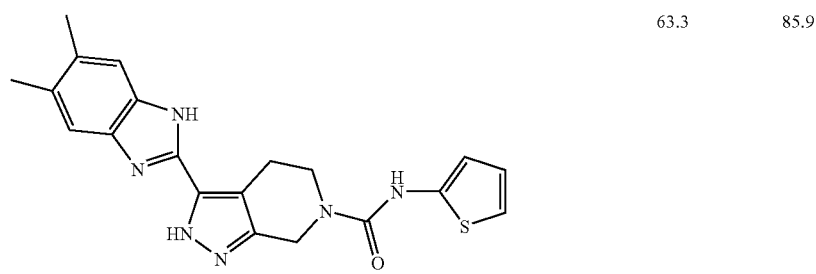 Chemistry 65 | 63.3 | 85.9 |

-continued
| Chemistry | KDR % Inhib. 10 μM | Tie2 % Inhib. 10 μM |
|---|---|---|
| 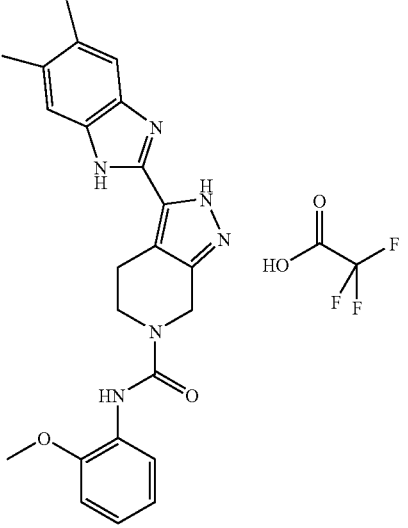  Chemistry 67 | 8.1 | 18.05 |
| 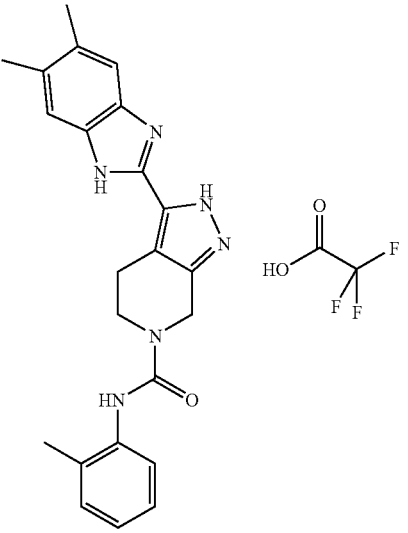  Chemistry 68 | 19.5 | 19.1 |
| 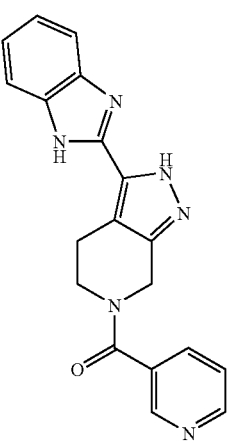  Chemistry 69 | 18.55 | 59.3 |

-continued
| Chemistry | KDR % Inhib. 10 μM | Tie2 % Inhib. 10 μM |
|---|---|---|
| 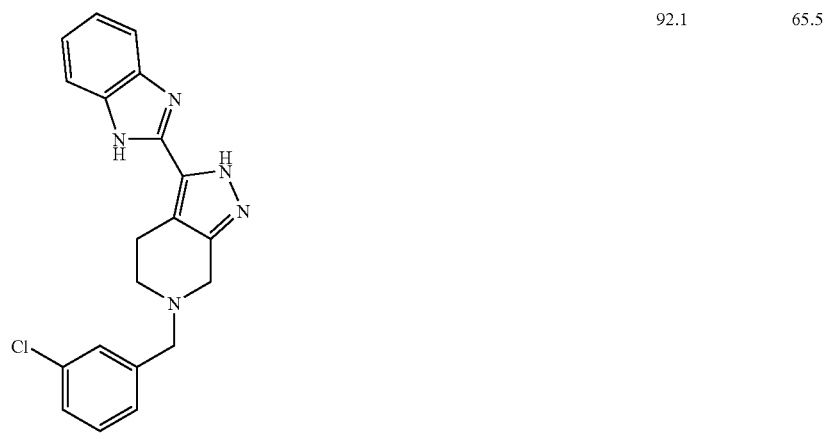 | 92.1 | 65.5 |ам
Chemistry 70
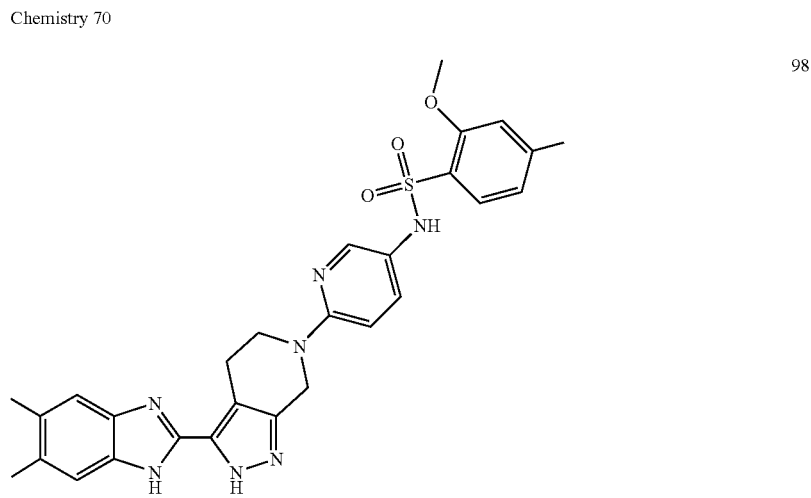
98
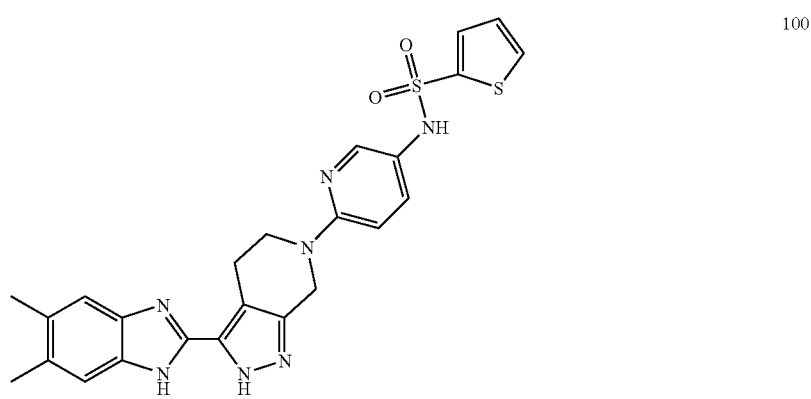
100

| Chemistry | KDR % Inhib. 10 μM | Tie2 % Inhib. 10 μM |
|---|---|---|

99

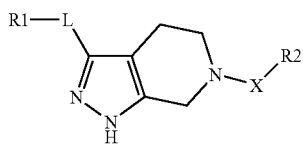

100

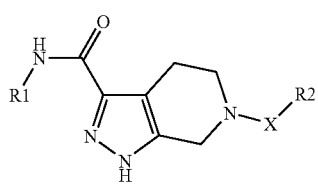

What is claimed is:

1. A compound of formula (I), including its tautomers:

(I)

$$R1-L-\text{[pyrazolo-tetrahydropyridine]}-N-X-R2$$

wherein:

L is chosen from $CH_2$, CO, $SO_2$, COO, NHCO, $NHSO_2$, and $NHCH_2$;

X is chosen from a bond, $CH_2$, CO, $SO_2$, CONH and COO;

R1 is OH or H, or is chosen from alkyl, cycloalkyl, heterocycle, aryl, heteroaryl, all of which is optionally substituted, and, when X is a bond, then R1 may also be halogen;

R2 is H or is chosen from alkyl, alkylene, cycloalkyl, heterocycle, aryl, heteroaryl, all of which is optionally substituted;

and in that the optional substituents are chosen independently from R3, O—R3, halogen, $NO_2$, $SO_2$—R3, CO—R3, $SO_2NH$—R3, CONH—R3, N—$(R3)_2$, NHCO—R3, $NHSO_2$—R3, NHCONH—R3, $NHSO_2NH$—R3, OCO—R3, COO—R3, $OSO_2$—R3, $SO_2O$—R3, OCONH—R3 and $OSO_2NH$—R3, wherein R3 is H or is chosen independently from alkyl, cycloalkyl, alkenyl, aryl, heteroaryl, heterocycle, all of which is optionally substituted with halogen, aryl, heteroaryl, R4, OR4 or $N(R4)_2$, wherein each R4 is chosen independently from H, $C_1$-$C_4$ alkyl and halogenated $C_1$-$C_4$ alkyl, or a racemate, a stereoisomer, an enantiomer, or a mixture in any combination thereof, or a pharmaceutically acceptable salt thereof.

2. The compound as set forth in claim 1, which is of the formula (III):

(III)

and its tautomers, wherein:

X is chosen from a bond, $CH_2$, CO, $SO_2$, CONH and COO;

R1 is chosen from alkyl, cycloalkyl, heterocyclyl, aryl, heteroaryl, all of which is optionally substituted;

R2 is H or is chosen from alkyl, alkylene, cycloalkyl, heterocycle, aryl, heteroaryl, all of which is optionally substituted;

and in that the optional substituents are chosen independently from R3, O—R3, halogen, $NO_2$, $SO_2$—R3, CO—R3, $SO_2NH$—R3, CONH—R3, N—$(R3)_2$, NH—CO—R3, NH—$SO_2$—R3, NHCONH—R3, $NHSO_2NH$—R3, OCO—R3, COO—R3, $OSO_2$—R3, $SO_2O$—R3, OCONH—R3 and $OSO_2NH$—R3, wherein each R3 is H or is chosen independently from alkyl, cycloalkyl, alkenyl, aryl, heteroaryl, heterocycle, all of which is optionally substituted with halogen, aryl, heteroaryl, OR4 or N(R4)2, and wherein each R4 is chosen independently from H and $C_1$-$C_4$ alkyl, or a racemate, a stereoisomer, an enantiomer, or a mixture in any combination thereof, or a pharmaceutically acceptable salt thereof.

3. The compound as set forth in claim 2, wherein R1 is heteroaryl, which is optionally substituted.

4. The compound as set forth in claim 1, wherein R1-L is R1-NH—CO.

5. The compound as set forth in claim 4, wherein R1 is H.

6. The compound as set forth in claim 4, wherein X is a bond, and R2 is chosen from substituted aryl and substituted heteroaryl.

7. The compound as set forth in claim 5, wherein X is a bond, and R2 is chosen from substituted aryl and substituted heteroaryl.

8. The compound as set forth in claim 7, wherein R2 is chosen from:
   aryl substituted with $NHSO_2$—R3 or NHCONH—R3, and heteroaryl substituted with $NHSO_2$—R3 or NHCONH—R3,
   wherein each R3 is H or is chosen independently from alkyl, cycloalkyl, alkenyl, aryl, heteroaryl, heterocycle, all of which is optionally substituted with halogen, aryl, heteroaryl, OR4 or $N(R4)_2$, and wherein each R4 is chosen independently from H, $C_1$-$C_4$ alkyl and halogenated $C_1$-$C_4$ alkyl.

9. The compound as set forth in claim 8, wherein aryl is phenyl, and heteroaryl is chosen from pyridyl and pyrimidyl.

10. The compound as set forth in claim 8, wherein R3 is chosen from substituted aryl and substituted heteroaryl.

11. The compound as set forth in claim 10, wherein R3 is substituted with a substituent selected from the group consisting of halogen, R4, OR4 and $N(R4)_2$, wherein each R4 is chosen independently from H, $C_1$-$C_4$ alkyl and halogenated $C_1$-$C_4$ alkyl.

* * * * *